United States Patent
Kitagawa et al.

(10) Patent No.: US 8,604,253 B2
(45) Date of Patent: Dec. 10, 2013

(54) METHOD FOR PRODUCING POLYHYDRIC PHENOL

(75) Inventors: Hideo Kitagawa, Kawasaki (JP); Junya Kiyosu, Kawasaki (JP); Susumu Saito, Chiba (JP); Takaomi Hayashi, Chiba (JP); Naritoshi Yoshimura, Funabashi (JP); Aya Nakagawa, Sodegaura (JP)

(73) Assignee: Mitsui Chemicals, Inc., Minato-Ku, Tokyo (JP)

( * ) Notice: Subject to any disclaimer, the term of this patent is extended or adjusted under 35 U.S.C. 154(b) by 134 days.

(21) Appl. No.: 13/266,393

(22) PCT Filed: Apr. 27, 2010

(86) PCT No.: PCT/JP2010/003022
§ 371 (c)(1),
(2), (4) Date: Oct. 26, 2011

(87) PCT Pub. No.: WO2010/125807
PCT Pub. Date: Nov. 4, 2010

(65) Prior Publication Data
US 2012/0046498 A1 Feb. 23, 2012

(30) Foreign Application Priority Data

Apr. 28, 2009 (JP) .............................. 2009-108995
Jun. 4, 2009 (JP) .............................. 2009-135375
Jun. 4, 2009 (JP) .............................. 2009-135380

(51) Int. Cl.
*C07C 37/07* (2006.01)

(52) U.S. Cl.
USPC ........................................ 568/763; 568/772

(58) Field of Classification Search
None
See application file for complete search history.

(56) References Cited

U.S. PATENT DOCUMENTS

| 4,218,401 A | 8/1980 | Wymore |
| 8,378,146 B2 * | 2/2013 | Suzuki et al. ................ 568/338 |
| 2011/0034735 A1 | 2/2011 | Suzuki et al. |

FOREIGN PATENT DOCUMENTS

| DE | 2 019 196 A1 | 11/1970 |
| WO | WO 2009/125581 A1 | 10/2009 |

OTHER PUBLICATIONS

Extended European Search Report dated Jan. 2, 2013, issued by European Patent Office in corresponding European Patent Application No. 10769507.4. (7 pages).
Schulz, M. et al., "α-Oxidation of Ketones Using N-Cation Radicals", Tetrahedron, vol. 46, No. 7, pp. 2371-2380 (Jan. 1, 1990) XP028088015.
International Search Report (PCT/ISA/210) issued on Jun. 1, 2010, by Japanese Patent Office as the International Searching Authority for International Application No. PCT/JP2009/003022.
C. Hansen et al., "Deoxygenation of Polyhydroxybenzenes: An Alternative Strategy for the Benzene-Free Synthesis of Aromatic Chemicals," J. Am. Chem. Soc., 2002, pp. 5926-5927, vol. 124.

(Continued)

*Primary Examiner* — Brian J Davis
(74) *Attorney, Agent, or Firm* — Buchanan Ingersoll & Rooney PC

(57) ABSTRACT

The present invention is a method for producing a polyhydric phenol, including the following steps (a) to (d): (a) a first step of producing (4S,5R,6S)-4,5,6-trihydroxy-2-cyclohexene-1-one from 2-deoxy-scyllo-inosose by a dehydration reaction; (b) a second step of producing 1,2,4-trihydroxybenzene from the (4S,5R,6S)-4,5,6-trihydroxy-2-cyclohexene-1-one obtained in the first step by a dehydration reaction; (c) a third step of producing 4-hydroxycyclohexane-1,3-dione from the 1,2,4-trihydroxybenzene by a catalytic hydrogenation reaction with the use of a metal catalyst; and (d) a fourth step of producing hydroquinone by heating the 4-hydroxycyclohexane-1,3-dione.

36 Claims, 1 Drawing Sheet

(56) References Cited

OTHER PUBLICATIONS

V. Zeitsev et al., "Synthesis of 2-Acyl-4-hydroxycyclohexane-1,3-diones, Kairomones and Defensive Compounds of Some Insects," Tetrahedron, 1994, pp. 6377-6386, vol. 50, No. 21.

Vestsi Akad. Navuk BSSR. Ser. Khim. navuk., 1990, pp. 67-71, vol. 1.

W. Reichenbecher et al., "Hydroxyhydroquinone reductase, the initial enzyme involved in the degradation of hydroxyhydroquinone (1,2,4-trihydroxybenzene) by *Desulfovibrio inopinatus*," Arch Microbiol, 2000, pp. 206-212, vol. 173.

K. Kakinuma et al., "An expeditious chemo-enzymatic route from glucose to catechol by the use of 2-deoxy-*scyllo*-inosose synthase," Tetrahedron Letters, 2000, pp. 1935-1938, vol. 41, No. 12.

Sharma et al., Cobalt phthalocyanine catalyzed aerobic oxidation of secondary alcohols: an efficient and simple synthesis of ketones, Tetetrahedron Letters 44 (2003), pp. 383-386.

Office Action issued in corresponding Korean Application No. 10-2011-7027636 dated Apr. 30, 2013.

\* cited by examiner

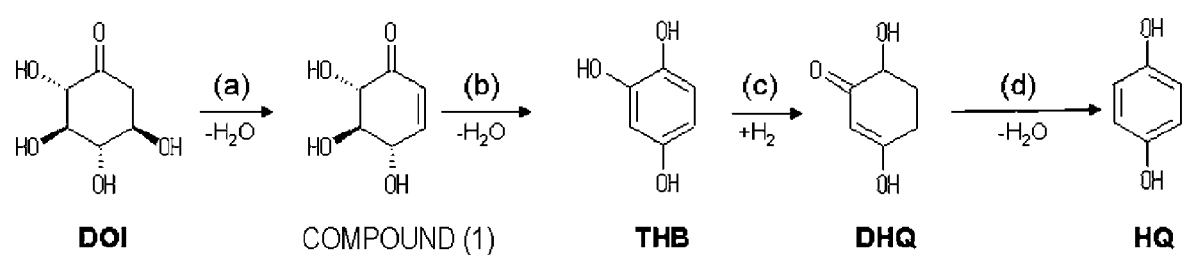

METHOD FOR PRODUCING POLYHYDRIC PHENOL

TECHNICAL FIELD

The present invention relates to a method for producing a polyhydric phenol.

BACKGROUND ART

Hydroquinone is a dihydric phenol having two hydroxyl groups on a benzene ring, which is an important compound as industrial chemicals such as a polymerization inhibitor, a photographic developing agent and a dye intermediate (a pigment or the like), or raw materials of a medicine, an agricultural chemical, a flavor material or the like. Meanwhile, 1,2,4-trihydroxybenzene is a trivalent phenol having three hydroxyl groups on a benzene ring, which is an important compound as an industrial chemical of an oxygen absorber or the like, or a raw material of a medicine, an agricultural chemical or the like. At present, tens of thousands of tons of these polyhydric phenols have been annually manufactured using petroleum as a raw material. However, in view of the present condition of global environment pollution, it is imperative to develop a novel production method which does not depend on petroleum.

Non-Patent Document 1 discloses a technology for producing 1,2,4-trihydroxybenzene (hereinafter referred to as THB) and hydroquinone by a chemical method using 2-deoxy-scyllo-inosose (hereinafter referred to as DOI) as a starting material. Non-Patent Document 1 discloses that THB is generated from DOI by heating under reflux in 0.5M phosphoric acid, and the obtained THB is catalytically reduced and dehydrated to obtain hydroquinone. According to the document, THB is obtained from DOI at a yield of 39%, and hydroquinone is obtained from THB at a yield of 53%.

Non-Patent Document 2 discloses a method for producing 4-hydroxycyclohexane-1,3-dione (hereinafter referred to as DHQ) from THB. According to this method, DHQ is obtained at a yield of 70% and a purity of 90% by HPLC analysis.

Non-Patent Document 3 discloses a method for producing hydroquinone from DHQ. According to this method, hydroquinone is obtained at a yield of 80%.

Non-Patent Document 4 discloses a method for producing DHQ from THB, not by a chemical method, but an enzymatic method. In Non-Patent Document 4, the yield of DHQ is not clearly stated.

RELATED DOCUMENTS

Non-Patent Documents

Non-Patent Document 1: J. Am. Chem. Soc., 2002, 124, 5926-5927

Non-Patent Document 2: Tetrahedron, Vol. 50, No. 21, 6377-6386, 1994

Non-Patent Document 3: Vestsi Akad. Navuk BSSR. Ser. khim. navuk., 1990, 1, 67-71

Non-Patent Document 4: Arch Microbiol, 2000, 173, 206-212

DISCLOSURE OF THE INVENTION

However, in the related arts as described in the above documents, as a method for industrially producing hydroquinone according to a chemical method, there is room for improvement in view of the yield. In particular, in a step of obtaining THB from DOI, it has been expected to further improve the yield.

The present invention has been accomplished in view of the above circumstances. An object of the present invention is to provide THB and hydroquinone which can be industrially produced using a chemical method.

According to the present invention, there is provided a method for producing a polyhydric phenol from 2-deoxy-scyllo-inosose, including the following steps (a) to (d):

(a) a first step of producing a compound represented by the following formula (1) from 2-deoxy-scyllo-inosose by a dehydration reaction;

(b) a second step of producing 1,2,4-trihydroxybenzene from the compound represented by the above formula (1) obtained in the above first step by a dehydration reaction;

(c) a third step of producing 4-hydroxycyclohexane-1,3-dione or a salt thereof from the 1,2,4-trihydroxybenzene by a catalytic hydrogenation reaction with the use of a metal catalyst; and (d) a fourth step of producing hydroquinone by heating the 4-hydroxycyclohexane-1,3-dione or the salt thereof,

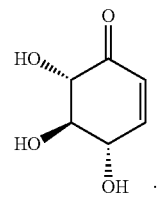

(1)

According to the present invention, in the reaction to obtain THB from DOI, the amount of a by-product may be reduced by carrying out a dehydration reaction with the use of the compound represented by the above formula (1) as the reaction intermediate. Accordingly, THB and hydroquinone can be industrially produced with using the chemical method.

In the present invention, the polyhydric phenol refers to a compound having at least two or more hydroxyl groups bonded to a benzene ring, and THB and hydroquinone are included in the polyhydric phenol.

DHQ used in the present invention represents a typical canonical structure, for example, may be a structure of 3,6-dihydroxyhexa-2-enone, or other tautomers.

According to the present invention, there is provided a chemical production method of THB and hydroquinone suitable for industrial production.

BRIEF DESCRIPTION OF THE DRAWINGS

The above and other objects, advantages and features of the present invention will be more apparent from the following description of certain preferred embodiments taken in conjunction with the accompanying drawings.

FIG. 1 is a view illustrating a reaction formula of a method for producing hydroquinone according to the present invention.

DESCRIPTION OF EMBODIMENTS

FIG. 1 is a view illustrating a reaction formula of a method for producing a polyhydric alcohol according to the present invention. (a) is a first step of producing a compound represented by the formula (1) from DOI by a dehydration reaction, (b) is a second step of producing THB from the compound represented by the formula (1) obtained in the first step by a dehydration reaction, (c) is a third step of producing DHQ or a salt thereof from THB by a catalytic hydrogenation reaction with the use of a metal catalyst, and (d) is a fourth step of producing hydroquinone by heating the DHQ or the salt thereof.

First Embodiment

In this embodiment, the steps (a) and (b) of the present invention will be described in detail. That is, in this embodiment, the second step (b) of the present invention is carried out by a dehydration reaction in the absence of an acid catalyst. According to this method, in the reaction to obtain THB from DOI, the dehydration reaction is carried out in the absence of an acid catalyst using the compound represented by the above formula (1) as the reaction intermediate. Accordingly, the amount of the by-product generated in the presence of an acid catalyst may be reduced. Thus, THB can be industrially produced with using the chemical method.

In the method of this embodiment, it is preferable that the dehydration reaction is carried out while the compound represented by the above formula (1) is dissolved in a reaction solvent and heated at equal to or more than 120 degrees centigrade. The reaction temperature may be more preferably 120 to 200 degrees centigrade. As the reaction solvent, water may be used. The concentration of the compound in the formula (1) to be reacted may be preferably 1 to 40 weight %. The reaction time may be preferably 30 minutes to 12 hours.

The compound represented by the above formula (1) can be produced from DOI by the dehydration reaction in accordance with the step (a) of the present invention. As the reaction conditions in this case, the dehydration reaction is carried out in the absence of an acid catalyst while heating preferably at equal to or more than 80 degrees centigrade, and more preferably 80 to 200 degrees centigrade. Furthermore, as the reaction solvent, water may be used. The concentration of DOI to be reacted may be preferably 1 to 40 weight %. The reaction time may be preferably 30 minutes to 20 hours and more preferably 1 to 3 hours.

Furthermore, THB may be produced from DOI in one-pot. One-pot mentioned herein means that a plurality of reactions are carried out in the same reaction vessel, and specifically two molecules of water are eliminated from DOI. One molecule of water is eliminated from DOI to give the compound represented by the formula (1), while one molecule of water is further eliminated from the compound represented by the formula (1) to give THB.

The dehydration reaction is carried out in the absence of an acid catalyst while heating at equal to or more than 120 degrees centigrade as the reaction condition for obtaining THB from DOI in one-pot. The reaction temperature may be preferably 80 to 200 degrees centigrade, more preferably 120 to 200 degrees centigrade, and further preferably 150 to 200 degrees centigrade. As the reaction solvent, water may be preferably used. The concentration of DOI to be reacted may be preferably 1 to 40 weight %. The reaction time may be preferably 30 minutes to 12 hours and more preferably 1 to 3 hours.

In this embodiment, as the reaction solvent, a solvent with low amount of dissolved oxygen may be preferably used from the viewpoint of improvement of the yield. Specifically, the amount of dissolved oxygen may be preferably equal to or less than 0.1 mg/L, and more preferably equal to or less than 0.02 mg/L. A method of reducing the pressure, a method of substituting with inert gas or the like may be used as a method of deoxygenating a solvent. For example, helium, nitrogen, argon or the like may be used as the inert gas when a method of substituting with inert gas is used. The amount of dissolved oxygen may be sufficiently reduced with the use of a solvent aerated with inert gas for 1 to 20 hours.

Incidentally, in place of DOI, 2,3,4,5-tetrahydroxy-cyclohexane-1-one may also be used.

After completion of the reaction, THB may be isolated by concentrating by evaporation of the solvent under reduced pressure. The purity of the obtained THB may be increased by using a known purification method such as silica gel chromatography, recrystallization or the like.

Subsequently, the operational effect of this embodiment will be described. According to the method of this embodiment, in the reaction to obtain THB from DOI, the dehydration reaction is carried out in the absence of an acid catalyst using the compound represented by the above formula (1) as the reaction intermediate. Accordingly, the amount of the by-product generated in the presence of an acid catalyst may be reduced. Thus, THB can be industrially produced with using the chemical method.

As in the past, the present inventors have made it clear that when DOI or the compound represented by the above formula (1) is subjected to a dehydration reaction in the presence of an acid catalyst, a compound represented by the following formula (4) (hereinafter referred to as the dimer) is obtained. When the obtained THB is used as it is for the production of hydroquinone, there has been a problem such that the dimer is also catalytically reduced and dehydrated to produce a new by-product which is mixed into hydroquinone, thus lowering the purity of hydroquinone.

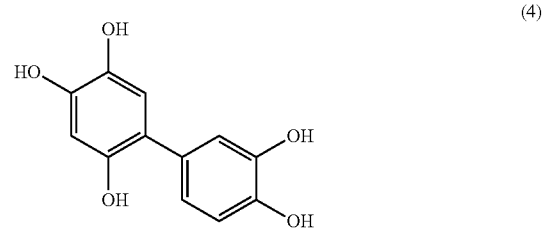 [SMILES: Oc1ccc(-c2cc(O)c(O)cc2O)cc1O]

(4)

However, in the method of this embodiment, the dehydration reaction is carried out in the absence of an acid catalyst. Then, generation of the dimer may be prevented. Accordingly, THB can be efficiently obtained.

Second Embodiment

In this embodiment, the third step (c) and the fourth step (d) of the present invention will be described in detail.

As mentioned above, as a method for producing hydroquinone by the chemical method industrially, there is room for improvement in view of the yield in the related arts as described in the above documents. For example, further improvement of the yield has been expected in the step of synthesizing hydroquinone from THB.

Non-Patent Document 1 does not disclose that DHQ is produced as an intermediate in the step of producing hydroquinone from THB. Also, each of the yield in the reaction to obtain DHQ from THB and the yield in the reaction to obtain hydroquinone from DHQ has not been specifically revealed.

Furthermore, the yield of DHQ in Non-Patent Document 2 becomes 63% in consideration of the purity as well. However, since the chemical method is adopted instead of the conventional oil method, further improvement of the yield has been desired.

In Non-Patent Document 3, the reaction temperature and the acid catalyst in use have not been specifically revealed.

Based on the contents described in Non-Patent Document 3, hydroquinone is not produced from DHQ.

In this embodiment, in the fourth step (d) of the present invention, a method for producing hydroquinone is provided, in which a step of heating DHQ in the presence of an aromatic compound is carried out, one of the heated aromatic compound or DHQ forms a salt, the aforementioned aromatic compound has at least one or more hydroxyl groups bonded to an aromatic ring.

According to the method of this embodiment, either of the aromatic compound having at least one or more hydroxyl groups bonded to an aromatic ring or DHQ forms a salt, and heated. Thus, the reaction for producing hydroquinone may proceed dominantly while suppressing the side reaction. Accordingly, hydroquinone can be produced industrially.

Hereinafter, this embodiment will be described in more detail.

This embodiment relates to a method for producing hydroquinone by carrying out the third step (c) and the fourth step (d) of the present invention. Specifically, the following step (c-1) as the third step (c) is carried out, and the following step (d-1) as the fourth step (d) is carried out:

(c-1) a step of producing DHQ from THB by the catalytic hydrogenation reaction with the use of a metal catalyst containing an iron group element as a metal component; and (d-1) a step of heating DHQ in the present of an aromatic compound salt.

Hereinafter, each step will be described in detail.

1. Step (c-1)

THB may be produced by using the method disclosed in Non-Patent Document 1, or may be produced by using the method described in the first embodiment.

The iron group element refers to iron, nickel and cobalt. In this embodiment, the metal component may be preferably nickel or cobalt, and particularly preferably nickel. Raney alloys such as Raney nickel, Raney cobalt and the like, or metal catalysts in which a metal component such as nickel, cobalt or the like is supported in a carrier are preferably used as the metal catalyst. Examples of the carrier include activated carbon, silica gel, alumina, graphite, diatomaceous earth, pumice, montmorillonite, zeolite and the like. Especially, alumina may be preferable. The amount of the metal supported may be usually in the range of 0.01 to 60 weight % and preferably in the range of 0.3 to 50 weight %, relative to the carrier. The amount of the catalyst added may be preferably 0.01 to 20 weight %, relative to THB.

The catalytic hydrogenation reaction of this embodiment may be carried out in the presence of a basic compound. Thus, DHQ can be obtained as a salt. An inorganic basic compound, an organic basic compound, or a mixture thereof may be used as the basic compound. The inorganic basic compound may be selected from the group consisting of alkali metal, alkali earth metal, alkali metal hydroxide, alkali earth metal hydroxide and ammonium hydroxide. Examples of the alkali metal include lithium, sodium, potassium, rubidium, cesium and the like. Examples of the alkali earth metal include beryllium, magnesium, calcium, strontium, barium and the like. Examples of the alkali metal hydroxide include lithium hydroxide, sodium hydroxide, potassium hydroxide, rubidium hydroxide, cesium hydroxide and the like. Examples of the alkali earth metal hydroxide include beryllium hydroxide, magnesium hydroxide, calcium hydroxide, strontium hydroxide, barium hydroxide and the like. The organic basic compound may be selected from the group consisting of quaternary ammonium salt or quaternary phosphonium salt represented by the following formula (5), alkali metal alkoxide or alkali metal aryloxide represented by the following formula (6), and amine, cyclic amine or a nitrogen-containing heterocyclic compound represented by the following formula (7),

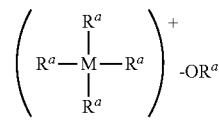

(5)

wherein, in the above formula (5), M represents a nitrogen atom or a phosphorus atom; and $R^a$ represents hydrogen, a linear or branched alkyl group having 1 to 12 carbon atoms, or a substituted or unsubstituted phenyl group, which may be the same or different from each other, excluding all $R^a$s of hydrogen, $$R^bOX \qquad (6)$$

wherein, in the above formula (6), $R^b$ represents a linear or branched alkyl group having 1 to 12 carbon atoms, or a substituted or unsubstituted phenyl group having 6 to 12 carbon atoms; and X represents lithium, sodium, potassium, rubidium or cesium, $$R^c{}_3N \qquad (7)$$

wherein, in the above formula (7), $R^c$ represents hydrogen, a linear or branched alkyl group having 1 to 12 carbon atoms, or a substituted or unsubstituted phenyl group, which may be the same or different from each other, excluding all $R^c$s of hydrogen.

Examples of the quaternary ammonium salt represented by the above formula (5) include methylammonium hydroxide, dimethylammonium hydroxide, trimethylammonium hydroxide, tetramethylammonium hydroxide, ethylammonium hydroxide, diethylammonium hydroxide, triethylammonium hydroxide, tetraethylammonium hydroxide, butylammonium hydroxide, dibutylammonium hydroxide, tributylammonium hydroxide, tetrabutylammonium hydroxide, tetrahexylammonium hydroxide, tetraoctylammonium hydroxide, tetrabutylammonium methoxide, tetrabutylammonium ethoxide, tetrabutylammonium butoxide and the like.

Examples of the quaternary phosphonium salt represented by the above formula (5) include tetramethylphosphonium hydroxide, tetraethylphosphonium hydroxide, tetrabutylphosphonium hydroxide, tetraphenylphosphonium hydroxide and the like.

Examples of the alkali metal alkoxide represented by the above formula (6) include lithium methoxide, sodium methoxide, potassium methoxide, rubidium methoxide, cesium methoxide, lithium ethoxide, sodium ethoxide, potassium ethoxide, rubidium ethoxide, cesium ethoxide, lithium propoxide, sodium propoxide, potassium propoxide, rubidium propoxide, cesium propoxide, lithium isopropoxide, sodium isopropoxide, potassium isopropoxide, rubidium isopropoxide, cesium isopropoxide, lithium butoxide, sodium butoxide, potassium butoxide, rubidium butoxide, cesium butoxide, sodium-t-butoxide, potassium-t-butoxide and the like. Examples of the alkali metal aryloxide represented by the above formula (6) include lithium phenoxide, sodium phenoxide, potassium phenoxide, rubidium phenoxide, cesium phenoxide, lithium salt of o-cresol, sodium salt of o-cresol, potassium salt of o-cresol, rubidium salt of o-cresol, cesium salt of o-cresol, lithium slat of m-cresol, sodium salt of m-cresol, potassium slat of m-cresol, rubidium salt of m-cresol, cesium slat of m-cresol, lithium salt of p-cresol, sodium salt of p-cresol, potassium salt of p-cresol, rubidium salt of p-cresol, cesium salt of p-cresol, lithium salt of catechol, sodium salt of catechol, potassium salt of catechol, rubidium salt of catechol, cesium salt of catechol, lithium salt of resorcinol, sodium salt of resorcinol, potassium salt of resorcinol, rubidium salt of resorcinol, cesium salt of resorcinol, lithium salt of hydroquinone, sodium salt of hydroquinone, potassium salt of hydroquinone, rubidium salt of hydroquinone, cesium salt of hydroquinone, lithium salt of 1,2,3-trihydroxybenzene, sodium salt of 1,2,3-trihydroxybenzene, potassium salt of 1,2,3-trihydroxybenzene, rubidium salt of 1,2,3-trihydroxybenzene, cesium salt of 1,2,3-trihydroxybenzene, lithium salt of 1,2,4-trihydroxybenzene, sodium salt of 1,2,4-trihydroxybenzene, potassium salt of 1,2,4-trihydroxybenzene, rubidium salt of 1,2,4-trihydroxybenzene, cesium salt of 1,2,4-trihydroxybenzene, lithium salt of 1,3,5-trihydroxybenzene, sodium salt of 1,3,5-trihydroxybenzene, potassium salt of 1,3,5-trihydroxybenzene, rubidium salt of 1,3,5-trihydroxybenzene, cesium salt of 1,3,5-trihydroxybenzene, lithium salt of 1-naphthol, sodium salt of 1-naphthol, potassium salt of 1-naphthol, rubidium salt of 1-naphthol, cesium salt of 1-naphthol, lithium salt of 2-naphthol, sodium salt of 2-naphthol, potassium salt of 2-naphthol, rubidium salt of 2-naphthol, cesium salt of 2-naphthol and the like.

Examples of the amine represented by the above formula (7) include methylamine, dimethylamine, trimethylamine, ethylamine, diethylamine, triethylamine, propylamine, dipropylamine, isopropylamine, diisopropylamine, diisopropylethylamine, butylamine, dibutylamine, tributylamine and the like. Furthermore, examples of the cyclic amine represented by the above formula (7) include aziridine, azetidine, pyrrolidine, piperidine, morpholine, quinuclidine and the like. Examples of the nitrogen-containing heterocyclic compound represented by the above formula (7) include pyrrole, pyridine, pyridazine, pyrimidine, pyrazine, oxazole, isoxazole, thiazole, isothiazole, imidazole, pyrazole, triazole, tetrazole, imidazoline, DBU (1,8-diazabicyclo[5,4,0]undecene-7) and the like.

THB may be preferably dissolved in a solvent. Water, or a linear or branched aliphatic alcohol having 1 to 12 carbon atoms may be used as the solvent. Methanol, ethanol, propanol, 1-butanol, 2-butanol, tertiary butanol, pentanol, octanol, decanol and dodecanol may be used as the aliphatic alcohol having 1 to 12 carbon atoms. Particularly water may be preferable as the solvent from the viewpoint of environmental protection. The concentration of THB to be reacted may be preferably 1 to 50 weight %, more preferably 2 to 40 weight %, further preferably 2 to 30 weight %, and particularly preferably 10 to 30 weight % from the viewpoint of efficient industrial production. When the lower limit is equal to or more than 1 weight %, the reaction volume is not increased much. On the other hand, when the upper limit is equal to or less than 50 weight %, the solution viscosity is not increased much. So, it is more suitable for industrial production.

In this embodiment, a solvent with low amount of dissolved oxygen may be preferably used as the reaction solvent from the viewpoint of improvement of the yield. Specifically, the amount of dissolved oxygen may be preferably equal to or less than 0.1 mg/L, and more preferably equal to or less than 0.02 mg/L. As a method of deoxygenating a solvent, the method described in the first embodiment may be used.

Any gas mixture containing hydrogen which is free from catalyst poisons such as carbon monoxide or hydrogen sulfide may be used as the hydrogenated gas. Such a gas mixture may be mixed with inert gas. Hydrogen having a purity of equal to or more than 95% may be preferably used, and hydrogen having a purity of equal to or more than 98% may be particularly preferably used. For example, nitrogen or argon may be used as the inert gas component. The hydrogen pressure may be preferably 0.1 to 15 MPa and particularly preferably 0.2 to 10 MPa. The reaction under the mild conditions is preferable because the side reaction is suppressed, and generation of the by-product may be suppressed. Therefore, the reaction temperature in the catalytic hydrogenation reaction may be preferably equal to or more than 10 degrees centigrade and equal to or less than the boiling point of the solvent. In case of the reaction with using water as a solvent, the reaction temperature may be preferably 10 to 100 degrees centigrade and more preferably 20 to 80 degrees centigrade. The reaction time may be preferably 1 to 100 hours.

After completion of the reaction, DHQ or a salt thereof can be obtained by replacing the inside of the reaction system with inert gas and removing the metal catalyst through filtration using filter paper, celite or the like. Thereafter, DHQ is prepared from a DHQ salt by neutralizing, as necessary, and DHQ may be isolated by carrying out liquid-liquid extraction.

2. Step (d-1)

In the step (d-1), the salt of the aromatic compound having at least one or more hydroxyl groups bonded to an aromatic ring is used. The salt of the aromatic compound can be prepared by mixing an aromatic compound having at least one or more hydroxyl groups bonded to an aromatic ring and a basic compound. The aromatic compound which is used for the preparation preferably includes an aromatic compound having 1 to 3 hydroxyl groups bonded to an aromatic ring, and more preferably includes an aromatic compound having two hydroxyl groups bonded to an aromatic ring. Examples of the aromatic compound having one hydroxyl group include phenol, o-cresol, m-cresol, p-cresol, 1-naphthol, 2-naphthol and the like. Examples of the aromatic compound having two hydroxyl groups include catechol, hydroquinone, resorcinol and the like. Examples of the aromatic compound having three hydroxyl groups include 1,2,3-trihydroxybenzene, 1,2,4-trihydroxybenzene (THB) and 1,3,5-trihydroxybenzene. The basic compound which is used for the preparation may be selected from the group consisting of alkali metal, alkali earth metal, alkali metal hydroxide, alkali earth metal hydroxide and ammonium hydroxide. Examples of the alkali metal include lithium, sodium, potassium, rubidium, cesium and the like. Examples of the alkali earth metal include beryllium, magnesium, calcium, strontium, barium and the like. Examples of the alkali metal hydroxide include lithium hydroxide, sodium hydroxide, potassium hydroxide, rubidium hydroxide, cesium hydroxide and the like. Examples of the alkali earth metal hydroxide include beryllium hydroxide, magnesium hydroxide, calcium hydroxide, strontium hydroxide, barium hydroxide and the like. The aromatic compound salts prepared like this way, particularly preferably include an alkali metal salt of an aromatic compound selected from the group consisting of phenol, catechol, hydroquinone, resorcinol, 1,2,3-trihydroxybenzene, 1,2,4-trihydroxybenzene (THB) and 1,3,5-trihydroxybenzene. A sodium salt thereof may be further preferable.

The step (d-1) may further include a step of mixing the aromatic compound salt with DHQ. For example, in this mixing step, the hydroquinone salt is mixed with DHQ as the aromatic compound salt, and then DHQ may be heated in the presence of the hydroquinone salt. Furthermore, in the step (d-1), DHQ may be dissolved in a solvent, and heated in a solution having the aromatic compound salt added thereto. Water, an aliphatic alcohol having 2 to 12 carbon atoms and an aprotic polar solvent may be preferably used as the reaction solvent. The aprotic polar solvent may be selected from the group consisting of an aliphatic nitrile having 2 to 12 carbon atoms, an aromatic nitrile, an aliphatic or alicyclic ether having 2 to 12 carbon atoms and a dialkyl ketone having 3 to 12 carbon atoms. Ethanol, propanol, 1-butanol, 2-butanol, tertiary butanol, pentanol, octanol, decanol and dodecanol are more preferable as the aromatic nitrile. Acetonitrile, propionitrile and butyronitrile may be more preferable as the aliphatic nitrile having 2 to 12 carbon atoms. Benzonitrile may be more preferable as the aromatic nitrile. Diisopropyl ether, tetrahydrofuran and dioxane may be more preferable as the aliphatic or alicyclic ether having 2 to 12 carbon atoms. Acetone, methyl ethyl ketone, 3-methyl-2-butanone, 2-pentanone, diethyl ketone, cyclopentanone, cyclohexanone, methyl isobutyl ketone, 3-methyl-2-pentanone, 2-methyl-3-pentanone, 3,3-dimethyl-2-butanone, 2-hexanone, 3-hexanone, isoamyl methyl ketone, 2-methyl-3-hexanone, 3-methyl-2-hexanone, 2-heptanone, 3-heptanone, 4-heptanone, 2,6-dimethyl-4-heptanone, ethyl isobutyl ketone, 5-methyl-3-heptanone, 2-octanone, 3-octanone, 2-nonanone and 5-nonanone are more preferable as the dialkyl ketone having 3 to 12 carbon atoms. Water may be particularly preferably used as the reaction solvent in order to reduce the environmental impact.

In this embodiment, a solvent with low amount of dissolved oxygen may be preferably used as the reaction solvent from the viewpoint of improvement of the yield. Specifically, the amount of dissolved oxygen may be preferably equal to or less than 0.1 mg/L, and more preferably equal to or less than 0.02 mg/L. The similar method as the manner described in the first embodiment may be used as a method of deoxygenating a solvent.

The amount of the aromatic compound salt in use is not limited, however, may be usually 10 to 200 weight parts, preferably 80 to 120 weight parts, and further preferably 100 weight parts, based on 100 weight parts of DHQ. Furthermore, in addition to the aforementioned aromatic compound salt, an aromatic compound without forming a salt of the same or different kind may coexist. In this case, the amount of the aromatic compound to coexist is not limited, however, may be usually 1 to 500 weight parts, preferably 50 to 450 weight parts, and further preferably 100 to 400 weight parts, based on 100 weight parts of DHQ. The concentration of DHQ to be reacted may be preferably 0.5 to 30 weight % and more preferably 1 to 20 weight %. The heating temperature may be preferably equal to or more than 120 degrees centigrade. The upper limit of the heating temperature is not particularly limited, however, may be preferably equal to or less than 300 degrees centigrade, more preferably equal to or less than 250 degrees centigrade, and further preferably equal to or less than 220 degrees centigrade. The lower limit of the heating temperature is not particularly limited, however, may be preferably equal to or more than 120 degrees centigrade, and more preferably equal to or more than 140 degrees centigrade. In this manner, the side reaction can be reduced, and the amount of the compound represented by the following formula (8) or (9) can be reduced,

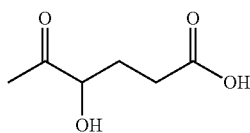

(8)

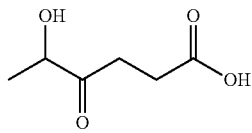

(9)

The reaction time may be preferably 1 minute to 30 hours, more preferably 10 minutes to 20 hours, and particularly preferably 15 minutes to 10 hours.

Incidentally, a solid acid catalyst represented by the following formula (3) may coexist along with the aromatic compound, $$[(M^b)_{2/p}O]_q \cdot Al_2O_3 \cdot [rSiO_2 \cdot tH_2O]_q \quad (3)$$

wherein, in the above formula (3), $M^b$ is a metal atom selected from the group consisting of Na, K, Ca and Ba; p is 1 or 2; q is 0 or 1; r is 2 to 10; and t is 2 to 7.

Examples of the solid acid catalyst represented by the above formula (3) include zeolite and alumina. Examples of zeolite include A, β, L, T, X, Y, ZSM-5, mordenite, chabazite, erionite and the like.

A solid acid catalyst containing a compound represented by the following formula (10) or a hydrate thereof may coexist along with the aromatic compound, $$(Na, Ca)_{1/3}(Al, Mg)_2[(OH)_2|Si_4O_{10}] \quad (10)$$

Examples of the solid acid catalyst represented by the above formula (10) include activated clay, montmorillonite and the like.

After completion of the reaction, the acid is added if necessary, and the resulting mixture is concentrated by evaporation of the solvent under reduced pressure, thereby isolating hydroquinone. The purity of the obtained hydroquinone may be increased by using a known purification method such as silica gel chromatography, recrystallization or the like.

Subsequently, the operational effect of this embodiment will be described. According to this method, DHQ is heated in the presence of the salt of the aromatic compound having at least one or more hydroxyl groups bonded to an aromatic ring. Thus, the reaction for producing hydroquinone may proceed dominantly while suppressing the side reaction. Accordingly, hydroquinone can be produced industrially.

According to the method of the step (c-1), the catalytic hydrogenation reaction is carried out with the use of a metal catalyst containing an iron group element as a metal component. Namely, according to this method, the catalytic hydrogenation reaction is carried out with the use of an iron group metal catalyst without using a platinum group metal catalyst such as palladium, ruthenium or rhodium. The catalytic reduction reaction of hydrogen may proceed more mildly with the iron group metal, as compared to the platinum group metal. Accordingly, DHQ can be produced from THB with a good yield. Nickel or cobalt is a metal with a higher Clarke number as compared to the platinum group metal. Accordingly, such metals can be available at a low cost, and a method more suitable for industrial production may be achieved.

Non-Patent Document 3 discloses that hydroquinone is produced from DHQ in the presence of an acid catalyst. However, the method described in Non-Patent Document 3 was inferior in reproducibility, and was not suitable for industrial production. According to knowledge of the present inventors, it has been found that the reaction for producing hydroquinone from DHQ by the dehydration reaction with the use of an acid catalyst under a low temperature condition such as about 80 to 100 degrees centigrade is carried out to proceed the side reaction dominantly. The structure of the product in this side reaction is not clear, but it is expected to proceed with the polymerization reaction of DHQ because a tar-like substance is produced after completion of the reaction.

Based on the above knowledge, the present inventors have repeatedly conducted an extensive study, thereby revealing that the reaction to produce hydroquinone proceeds dominantly if the reaction is carried out while heating DHQ in the presence of a salt of an aromatic compound having at least one or more hydroxyl groups bonded to an aromatic ring. Therefore, in the method of this embodiment, hydroquinone can be stably and efficiently produced, thereby making possible it to produce hydroquinone in large quantities industrially.

By the way, in this embodiment, either aromatic compound or DHQ to be heated may form a salt. Also, a salt of DHQ may be heated in the presence of an aromatic compound. The DHQ salt can be obtained by carrying out the catalytic hydrogenation reaction in the step (c-1) in the presence of a basic compound and removing the metal catalyst. Furthermore, the DHQ salt may be prepared by the addition of an inorganic basic compound selected from the group consisting of alkali metal, alkali earth metal, alkali metal hydroxide, alkali earth metal hydroxide and ammonium hydroxide to DHQ. In this case, an aromatic compound having at least one or more hydroxyl groups bonded to an aromatic ring may be preferable as the aromatic compound. An aromatic compound having 1 to 3 hydroxyl groups bonded to an aromatic ring may be more preferable. Further, an aromatic compound having two hydroxyl groups bonded to an aromatic ring may be more preferable. Examples of the aromatic compound having one hydroxyl group include phenol, o-cresol, m-cresol, p-cresol, 1-naphthol, 2-naphthol and the like. Examples of the aromatic compound having two hydroxyl groups include catechol, hydroquinone, resorcinol and the like. Examples of the aromatic compound having three hydroxyl groups include 1,2,3-trihydroxybenzene, THB and 1,3,5-trihydroxybenzene.

The DHQ salt may be dissolved in a reaction solvent if necessary, and heated with the addition of an aromatic compound. The same reaction solvent as described above may be used. The amount of the aromatic compound in use is not limited, however, may be usually 10 to 1,000 weight parts, preferably 50 to 750 weight parts, and further preferably 100 to 500 weight parts, based on 100 weight parts of the DHQ salt. Furthermore, as the aromatic compound, the compounds exemplified above may be used singly or two or more kinds may be used in combination. The amount of the aromatic compound in this case is not limited, however, may be usually 10 to 1,000 weight parts, preferably 50 to 750 weight parts, and further preferably 100 to 500 weight parts, based on 100 weight parts of the DHQ salt. The concentration of the DHQ salt to be reacted may be preferably 0.5 to 30 weight %, and more preferably 1 to 20 weight %. The heating temperature and the reaction time are the same as those illustrated above. As illustrated above, a solid acid catalyst may be added.

In this embodiment, in the step (d-1), mixing of the aromatic compound salt with DHQ before heating DHQ was exemplified. However, the aromatic compound and the DHQ salt may be mixed. For example, hydroquinone is mixed with the DHQ salt as the aromatic compound in this mixing step, and then the DHQ salt may be heated in the presence of hydroquinone. Furthermore, hydroquinone may be obtained from the DHQ salt by carrying out the step (d-1) again by mixing hydroquinone obtained in the step (d-1) with the DHQ salt obtained in the step (c-1). DHQ or the salt thereof used in the step (d-1) may be produced by using a known method as described, for example, in Non-Patent Document 2, not the step (c-1).

Third Embodiment

This embodiment relates to a method for producing hydroquinone using DOI as a starting material. This method includes, in addition to the steps (a) to (d) of the present invention, carrying out the steps (e) and (f). Specifically, the following steps of (a-1), (b-1), (c-2), (d-2), (e) and (f) are carried out in this order:

(a-1) a step of producing the compound represented by the above formula (1), that is, (4S,5R,6S)-4,5,6-trihydroxy-2-cyclohexene-1-one, from DOI by a dehydration reaction in the absence of an acid catalyst;

(b-1) a step of producing THB from the compound represented by the above formula (1) obtained in the step (a-1) by a dehydration reaction in the absence of an acid catalyst;

(c-2) a step of producing an alkali metal salt of DHQ from THB obtained in the step (b) by a catalytic hydrogenation reaction with the use of a metal catalyst containing an iron group element as a metal component in the presence of alkali metal hydroxide;

(d-2) a step of heating the alkali metal salt of DHQ obtained in the step (c-2) in the presence of an aromatic compound having at least one or more hydroxyl groups bonded to an aromatic ring;

(e) a step of mixing the alkali metal salt of DHQ produced in the step (c-2) with hydroquinone obtained in the step (d-2); and (f) a step of heating the alkali metal salt of DHQ in the presence of hydroquinone.

Each step will be described below.

1. Step (a-1): Step of producing (4S,5R,6S)-4,5,6-trihydroxy-2-cyclohexene-1-one from DOI In this step, the dehydration reaction is carried out while heating an aqueous solution of DOI at equal to or more than 80 degrees centigrade in the absence of an acid catalyst. The reaction temperature may be preferably 80 to 200 degrees centigrade. As the reaction solvent, water may be used. The reaction concentration (the concentration of DOI to be fed) may be preferably 1 to 40 weight %. The reaction time may be preferably 30 minutes to 20 hours, and more preferably 1 to 3 hours. (4S,5R,6S)-4,5,6-trihydroxy-2-cyclohexene-1-one may be isolated by using a known method, and the step (b-1) may be subsequently carried out.

In place of DOI, 2,3,4,5-tetrahydroxy-cyclohexane-1-one may be used.

2. Step (b-1): Step of producing THB from (4S,5R,6S)-4,5,6-trihydroxy-2-cyclohexene-1-one In this step, the dehydration reaction is carried out while heating an aqueous solution of (4S,5R,6S)-4,5,6-trihydroxy-2-cyclohexene-1-one obtained in the step (a-1) at equal to or more than 120 degrees centigrade in the absence of an acid catalyst. The step (b-1) may be carried out in the same manner as in the method described in the first embodiment.

Incidentally, the steps (a-1) and (b-1) may be carried out in one-pot according to the reaction conditions described in the first embodiment.

After completion of the dehydration reaction of (4S,5R,6S)-4,5,6-trihydroxy-2-cyclohexene-1-one, THB may be isolated by concentrating by evaporation of the solvent under reduced pressure. The purity of the obtained THB may be increased by using a known purification method such as silica gel chromatography, recrystallization or the like.

3. Step (c-2): Step of producing the alkali metal salt of DHQ from THB by a catalytic hydrogenation reaction with the use of a metal catalyst containing an iron group element as a metal component in the presence of alkali metal hydroxide After completion of the step (b-1), the obtained reaction solution is cooled if necessary, added alkali metal hydroxide and a metal catalyst, and then carried out the catalytic hydrogenation reaction in the same manner with the step (c-1) described in the second embodiment. The metal catalyst to be used may be a metal catalyst having nickel or cobalt as a metal component. For example, sodium hydroxide may be used as the alkali metal hydroxide. In this way, an alkali metal salt of DHQ can be produced. After the reaction, the metal catalyst is removed through filtration or the like, and the obtained aqueous solution of the alkali metal salt of DHQ is used as it is for carrying out the next step.

4. Step (d-2): Step of heating the alkali metal salt of DHQ in the presence of an aromatic compound The aqueous solution of the alkali metal salt of DHQ which is obtained in the step (c-2) is heated in the presence of an aromatic compound. In this case, an aromatic compound having at least one or more hydroxyl groups bonded to an aromatic ring may be preferable as the aromatic compound. For example, phenol, o-cresol, m-cresol, p-cresol, 1-naphthol, 2-naphthol, catechol, hydroquinone, resorcinol, 1,2,3-trihydroxybenzene, 1,2,4-trihydroxybenzene (THB), 1,3,5-trihydroxybenzene and the like may be used. The concentration of the DHQ salt may be preferably 0.5 to 30 weight %, and more preferably 1 to 20 weight %. If necessary, the reaction concentration may be adjusted by adding or concentrating the reaction solvent. As the reaction solvent, the same reaction solvents described in the step (d-1) of the second embodiment may be used. The reaction temperature and the reaction time may be the same as those described in the step (d-1) of the second embodiment.

5. Step (e): Step of mixing the alkali metal salt of DHQ with hydroquinone

An aqueous solution of the alkali metal salt of obtained DHQ is prepared by carrying out the steps (a-1), (b-1) and (c-2) in this order in another batch. The aqueous solution of the alkali metal salt of DHQ is mixed with all or part of hydroquinone obtained in the step (d-2). Thus, the reaction may be carried out in the same manner as in the step (d-1) described in the second embodiment using hydroquinone as the aromatic compound.

6. Step (f): Step of heating the alkali metal salt of DHQ in the presence of hydroquinone A mixture of hydroquinone and the alkali metal salt of DHQ obtained in the step (e) is heated. For example, the reaction may be carried out in the same manner as in the step (d-1) described in the second embodiment using hydroquinone as the aromatic compound.

In this embodiment, a solvent with low amount of dissolved oxygen may be preferably used as the reaction solvent through each step of (a-1), (b-1), (c-2), (d-2), (e) and (f). Specifically, the amount of dissolved oxygen may be preferably equal to or less than 0.1 mg/L, and more preferably equal to or less than 0.02 mg/L. As a method of deoxygenating a solvent, the similar method as the manner described in the first embodiment may be used.

Hydroquinone may be purified according to the method described in the second embodiment.

In the method of this embodiment, each step may be efficiently carried out from DOI. The reaction solvent used in all of the steps (a-1), (b-1), (c-2), (d-2), (e) and (f) is water, and the reagent in use may also be removed through filtration or the like. Furthermore, the reaction conditions may be controlled only with pH control and temperature control according to the acid-base reaction. Accordingly, the above steps (a-1) to (f) may be serially carried out without requiring a purification process, and such a method is excellent in industrial production.

Hereinafter, effects of each step will be described in detail. In the steps (a-1) and (b-1), in the reaction to obtain THB from DOI, the dehydration reaction is carried out in the absence of an acid catalyst using the compound represented by the above formula (1) as the reaction intermediate. Thus, the amount of the by-product generated in the presence of an acid catalyst may be reduced. Accordingly, THB can be industrially produced with using the chemical method.

As described in the first embodiment, the present inventors have made it clear that when DOI or the compound represented by the above formula (1) is subjected to a dehydration reaction in the presence of an acid catalyst, the dimer represented by the above formula (4) is obtained. When the obtained THB is used as it is for the production of hydroquinone, there has been a problem such that the dimer is also catalytically reduced and dehydrated to produce a new by-product which is mixed into hydroquinone, thus lowering the purity of hydroquinone.

However, in the method of this embodiment, the dehydration reaction is carried out in the absence of an acid catalyst. Thus, generation of the dimer may be prevented. Accordingly, THB can be efficiently obtained.

In the steps (c-2) and (d-2), the same effects as those described in the second embodiment may be achieved.

In the steps (e) and (f), the dehydration reaction of DHQ proceeds using hydroquinone produced in the step (d-2). So, the steps (e) and (f) may achieve a continuous process. Since hydroquinone may increase in production only with preparation of a small amount of aromatic compound, it is favorably used from the viewpoint of reduced cost by the reduced amount of the prepared reaction catalyst. Since hydroquinone acts as a catalyst in the dehydration reaction, the step of separating the produced hydroquinone from the reaction catalyst can be skipped. Therefore, the purification process can be simplified.

As described above, the method of this embodiment is excellent as a method for producing hydroquinone industrially.

Fourth Embodiment

In this embodiment, with respect to the fourth step (d) of the present invention, an example different from the second embodiment will be described.

Specifically, this embodiment relates to a method for producing hydroquinone including a step of heating DHQ at equal to or more than 120 degrees centigrade in the presence of a dehydration catalyst. The dehydration catalyst is an oxide catalyst, or an acid or base catalyst represented by the following formula (2), $$(M^a)_m X_n \tag{2}$$

wherein, in the above formula (2), $M^a$ is $H^+$, $Li^+$, $Na^+$, $K^+$, $Rb^+$, $Cs^+$, $Be^{2+}$, $Mg^{2+}$, $Ca^{2+}$, $Sr^{2+}$ or $Ba^{2+}$; X is sulfate ion, hydrogen sulfate ion, sulfite ion, hydrogen sulfite ion, phosphate ion, hydrogen phosphate ion, dihydrogen phosphate ion, perchlorate ion, hexafluorophosphate ion, an anion of an aliphatic or aromatic carboxylic acid having 1 to 12 carbon atoms, or an anion of an aliphatic or aromatic sulfonic acid having 1 to 12 carbon atoms; an anion of an aliphatic or aromatic carboxylic acid having 1 to 12 carbon atoms and an anion of an aliphatic or aromatic sulfonic acid having 1 to 12 carbon atoms may be respectively immobilized on a carrier; m is 1 to 3; and n is 1 to 3. Moreover, when $M^a$ and X are equivalent ions, each of m and n is 1. When $M^a$ is a monovalent cation and X is a divalent anion, m is 2 and n is 1. When $M^a$ is a monovalent cation and X is a trivalent anion, m is 3 and n is 1. When $M^a$ is a divalent cation and X is a monovalent anion, m is 1 and n is 2. When $M^a$ is a divalent cation and X is a trivalent anion, m is 3 and n is 2.

DHQ can be produced from THB by using a known method as described, for example, in Non-Patent Document 2. As described in Non-Patent Document 1, THB may be produced from DOI, and DHQ may be produced by the method as described in Non-Patent Document 2. Furthermore, they may be produced by the method as described in the step (c-1) of the second embodiment.

Although the details will be described later, in the step of this embodiment, the use of an oxide catalyst, or an acid or base catalyst represented by the above formula (2) as a dehydration catalyst make it possible to proceed the reaction for producing hydroquinone dominantly while suppressing the side reaction. In this embodiment, the oxide catalyst refers to a catalyst composed of a metal oxide, which includes a complex oxide combined several metal oxides. In this embodiment, an acid catalyst refers to a catalyst that the pH of water at 25 degrees centigrade, which is added a dehydration catalyst, is lower than 7. A base catalyst refers to a catalyst that the pH of the water is higher than 7.

A catalyst containing magnesium, aluminum, silicon, titanium, copper, zinc, zirconium, molybdenum or tungsten as the metallic element may be preferably used as the oxide catalyst used in the step of this embodiment. MgO, $Al_2O_3$, $SiO_2$, $TiO_2$, CuO, ZnO, $ZrO_2$, $MoO_3$, $WO_3$ or a hydrate thereof, or a composite oxide thereof may be more preferably used. More specifically, an oxide catalyst containing any one of aluminum and silicon may be further preferable. A solid acid catalyst containing a compound represented by the following formula (3) may be particularly preferable.

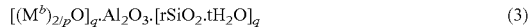

$[(M^b)_{2/p}O]_q \cdot Al_2O_3 \cdot [rSiO_2 \cdot tH_2O]_q$     (3)

wherein, in the above formula (3), $M^b$ is a metal atom selected from the group consisting of Na, K, Ca and Ba; p is 1 or 2; q is 0 or 1; r is 2 to 10; and t is 2 to 7.

Examples of the solid acid catalyst represented by the above formula (3) include zeolite and alumina. Examples of zeolite include A, β, L, T, X, Y, ZSM-5, mordenite, chabazite, erionite and the like.

As the oxide catalyst, a solid acid catalyst containing a compound represented by the following formula (10) or a hydrate thereof may be used,

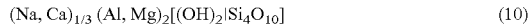

$(Na, Ca)_{1/3}(Al, Mg)_2[(OH)_2|Si_4O_{10}]$     (10)

Examples of the solid acid catalyst represented by the above formula (10) include activated clay, montmorillonite and the like.

An acid catalyst represented by the above formula (2) may be used as the dehydration catalyst. Specifically, the acid catalyst to be used may include inorganic acids such as sulfuric acid, sulfurous acid, phosphoric acid, perchloric acid, hexafluorophosphoric acid and the like; aliphatic carboxylic acids such as acetic acid, propionic acid, butanoic acid, hexanoic acid, heptanoic acid, octanoic acid, nonanoic acid, decanoic acid, didecanoic acid (lauric acid) and the like; aliphatic dicarboxylic acids such as oxalic acid, malonic acid, succinic acid, glutaric acid, adipic acid, sebacic acid and the like; aromatic carboxylic acids such as benzoic acid, toluic acid and the like; aromatic dicarboxylic acids such as isophthalic acid, terephthalic acid and the like; aliphatic sulfonic acids such as methanesulfonic acid, ethanesulfonic acid, propanesulfonic acid, hexanesulfonic acid, octanesulfonic acid, dodecanesulfonic acid and the like; and aromatic sulfonic acids such as benzenesulfonic acid, toluenesulfonic acid and the like.

An acid catalyst or a base catalyst may be used as the dehydration catalyst, in which all or part of proton ($H^+$) in the acid catalyst represented by the above formula (2) is neutralized by alkali metal or alkali earth metal. Examples of the alkali metal include lithium, sodium, potassium, rubidium, cesium and the like. Examples of the alkali earth metal include beryllium, magnesium, calcium, strontium, barium and the like. Specifically, examples of the acid catalyst or the base catalyst to be used may include alkali metal salt or alkali earth metal salt of an inorganic acid such as sulfuric acid, sulfurous acid, phosphoric acid, perchloric acid, hexafluorophosphoric acid or the like; alkali metal salt or alkali earth metal salt of an aliphatic carboxylic acid such as acetic acid, propionic acid, butanoic acid, hexanoic acid, heptanoic acid, octanoic acid, nonanoic acid, decanoic acid, didecanoic acid (lauric acid) or the like; alkali metal salt or alkali earth metal salt of an aliphatic dicarboxylic acid such as oxalic acid, malonic acid, succinic acid, glutaric acid, adipic acid, sebacic acid or the like; alkali metal salt or alkali earth metal salt of an aromatic carboxylic acid such as benzoic acid, toluic acid or the like; alkali metal salt or alkali earth metal salt of an aromatic dicarboxylic acid such as isophthalic acid, terephthalic acid or the like; alkali metal salt or alkali earth metal salt of an aliphatic sulfonic acid such as methanesulfonic acid, ethanesulfonic acid, propanesulfonic acid, hexanesulfonic acid, octanesulfonic acid, dodecanesulfonic acid or the like; and alkali metal salt or alkali earth metal salt of an aromatic sulfonic acid such as benzenesulfonic acid, toluenesulfonic acid or the like.

The dehydration catalyst described by the above formula (2), which X is an anion of an aliphatic or aromatic carboxylic acid having 1 to 12 carbon atoms, or an anion of an aliphatic or aromatic sulfonic acid having 1 to 12 carbon atoms may include an ion exchange resin in which a carbon atom in X is associated with a resin such as a mel field resin, a Wang resin, a trityl resin, a Rink resin or the like through a covalent bond.

The amount of the dehydration catalyst may be preferably equal to or more than 1 weight part and equal to or less than 1,000 weight parts, more preferably equal to or more than 10 weight parts and equal to less than 500 weight parts, and further preferably equal to or more than 20 weight parts and equal to or less than 300 weight parts, based on 100 weight parts of DHQ. In this way, the reaction for producing hydroquinone may proceed dominantly while suppressing the side reaction.

In the step of this embodiment, DHQ may be heated in a solution dissolved in a solvent. The dehydration catalyst may be dissolved in a solvent, or may not be dissolved in a solvent. The use of an insoluble dehydration catalyst such as a solid acid catalyst or a solid base catalyst makes it easy to separate hydroquinone from the dehydration catalyst. Therefore, such a catalyst has advantage to make purification treatment easy.

In this embodiment, a solvent with low amount of dissolved oxygen may be preferably used as the reaction solvent from the viewpoint of improvement of the yield. Specifically, the amount of dissolved oxygen may be preferably equal to or less than 0.1 mg/L, and more preferably equal to or less than 0.02 mg/L. The similar method as the manner described in the first embodiment may be used as a method of deoxygenating a solvent.

Water or any organic solvent can be used as the reaction solvent. An aliphatic alcohol having 2 to 12 carbon atoms and an aprotic polar solvent may be preferable used as the reaction solvent. The aprotic polar solvent may be selected from the group consisting of an aliphatic nitrile having 2 to 12 carbon atoms, an aromatic nitrile, an aliphatic or alicyclic ether having 2 to 12 carbon atoms and a dialkyl ketone having 3 to 12 carbon atoms. Examples of the aliphatic alcohol having 2 to 12 carbon atoms may more preferably include ethanol, propanol, 1-butanol, 2-butanol, tertiary butanol, pentanol, octanol, decanol and dodecanol. Examples of the aliphatic nitrile having 2 to 12 carbon atoms may more preferably include acetonitrile, propionitrile and butyronitrile. Examples of the aromatic nitrile may more preferably include benzonitrile. Examples of the aliphatic or alicyclic ether having 2 to 12 carbon atoms may more preferably include diisopropyl ether, tetrahydrofuran and dioxane. Examples of the dialkyl ketone having 3 to 12 carbon atoms may more preferably include acetone, methyl ethyl ketone, 3-methyl-2-butanone, 2-pentanone, diethyl ketone, cyclopentanone, cyclohexanone, methyl isobutyl ketone, 3-methyl-2-pentanone, 2-methyl-3-pentanone, 3,3-dimethyl-2-butanone, 2-hexanone, 3-hexanone, isoamyl methyl ketone, 2-methyl-3-hexanone, 3-methyl-2-hexanone, 2-heptanone, 3-heptanone, 4-heptanone, 2,6-dimethyl-4-heptanone, ethyl isobutyl ketone, 5-methyl-3-heptanone, 2-octanone, 3-octanone, 2-nonanone and 5-nonanone. Water may be particularly preferably used as the reaction solvent in order to reduce the environmental impact.

DHQ may be dissolved in a reaction solvent, and added to a dehydration catalyst, and then heated. The concentration of DHQ to be reacted may be preferably 0.5 to 30 weight %, and more preferably 1 to 20 weight %. The upper limit of the heating temperature is not particularly limited, however, may be preferably equal to or less than 300 degrees centigrade, more preferably equal to or less than 250 degrees centigrade, and particularly preferably equal to or less than 220 degrees centigrade.

The reaction time may be preferably 1 minute to 30 hours, more preferably 10 minutes to 20 hours, and particularly preferably 0.5 to 10 hours.

After completion of the reaction, the resulting mixture can be concentrated by evaporation of the solvent under reduced pressure, thereby isolating hydroquinone. The purity of the obtained hydroquinone may be increased by using a known purification method such as silica gel chromatography, recrystallization or the like.

Subsequently, the operational effect of this embodiment will be described. According to the method of this embodiment, DHQ is heated at equal to or more than 120 degrees centigrade in the presence of a dehydration catalyst. Thus, DHQ is exposed to a high temperature with a specific dehydration catalyst, thereby carrying out the dehydration reaction of DHQ dominantly while suppressing the side reaction. Accordingly, hydroquinone can be produced industrially.

As described already, Non-Patent Document 3 discloses that hydroquinone is produced from DHQ in the presence of an acid catalyst. However, the method described in Non-Patent Document 3 was poor-reproducible. Therefore, such a method cannot be adapted to industrial production. According to knowledge of the present inventors, it has been found that the reaction for producing hydroquinone with the use of DHQ under a low temperature condition such as about 80 to 100 degrees centigrade makes the side reaction proceed dominantly. The structure of the product in this side reaction is not clear, but it is expected to proceed with the polymerization reaction of DHQ because a tar-like substance is produced after completion of the reaction.

Based on the above knowledge, the present inventors have repeatedly conducted an extensive study, thereby revealing that the reaction for producing hydroquinone proceeds dominantly if the reaction is carried out while heating at equal to or more than 120 degrees centigrade. Also, the present inventors have revealed that the reaction for producing hydroquinone proceeds dominantly not only by simply increasing the reaction temperature, but also by using a selected specific dehydration catalyst. Thus, according to the method of this embodiment, hydroquinone can be stably and efficiently produced, thereby making it possible to produce in large quantities industrially.

Fifth Embodiment

This embodiment relates to a method for producing hydroquinone including a step of heating 4-hydroxycyclohexane-1,3-dione salt (DHQ salt) at equal to or more than 120 degrees centigrade in the presence of a dehydration catalyst. This method is the same as the fourth embodiment, except that the DHQ salt is used instead of DHQ. In this embodiment, the points different from the fourth embodiment will only be described, while the same explanation as the fourth embodiment will not be repeated.

The DHQ salt can be prepared by mixing DHQ with a basic compound. An inorganic basic compound, an organic basic compound or a mixture thereof may be used as the basic compound used for this preparation. The inorganic basic compound may be selected from the group consisting of alkali metal, alkali earth metal, alkali metal hydroxide, alkali earth metal hydroxide and ammonium hydroxide. Examples of the alkali metal include lithium, sodium, potassium, rubidium, cesium and the like. Examples of the alkali earth metal include beryllium, magnesium, calcium, strontium, barium and the like. Examples of the alkali metal hydroxide include lithium hydroxide, sodium hydroxide, potassium hydroxide, rubidium hydroxide, cesium hydroxide and the like. Examples of the alkali earth metal hydroxide include beryllium hydroxide, magnesium hydroxide, calcium hydroxide, strontium hydroxide, barium hydroxide and the like. Quaternary ammonium salt or quaternary phosphonium salt represented by the above formula (5), alkali metal alkoxide or alkali metal aryloxide represented by the above formula (6), and amine, cyclic amine or a nitrogen-containing heterocyclic compound represented by the above formula (7), as described in the second embodiment may be preferably used as the organic basic compound.

The amount of the basic compound as the mixing ratio of DHQ and a basic compound may be preferably 1.5 molar equivalents, more preferably 1.2 molar equivalents, and further preferably 1 molar equivalent, based on 1 molar equivalent of DHQ.

The DHQ salt can be prepared by dissolving DHQ in a solvent and adding a basic compound to the obtained DHQ solution. A reaction solvent in the dehydration reaction may be preferable as the solvent used herein. In this way, after the preparation of the DHQ salt, a dehydration solvent is added without extracting the DHQ salt from the reaction solution, and the dehydration reaction of the DHQ salt may be carried out. Thus, the use of the same solvent for the preparation of a DHQ salt with the solvent used in the dehydration reaction makes it possible to carry out such a preparation and such a reaction in one-pot.

The DHQ salt may be prepared by reacting with the basic compound while stirring DHQ in a solvent. The DHQ salt may be preferably prepared at 0 to 50 degrees centigrade.

The DHQ salt is prepared to have a concentration of preferably 0.5 to 30 weight % and more preferably 1 to 20 weight %.

In the method of this embodiment, the DHQ salt is heated at equal to or more than 120 degrees centigrade in the presence of a dehydration catalyst. Thus, the dehydration reaction of the DHQ salt may efficiently proceed. Accordingly, hydroquinone can be produced industrially.

Sixth Embodiment

This embodiment relates to a method for producing hydroquinone including the following steps:

(a-1) a step of producing the compound represented by the above formula (1), that is, (4S,5R,6S)-4,5,6-trihydroxy-2-cyclohexene-1-one, from DOI by a dehydration reaction in the absence of an acid catalyst;

(b-1) a step of producing THB from the (4S,5R,6S)-4,5,6-trihydroxy-2-cyclohexene-1-one obtained in the step (a-1) by a dehydration reaction in the absence of an acid catalyst;

(c-3) a step of producing DHQ or a salt thereof from THB obtained in the step (b-1) by a catalytic hydrogenation reaction with the use of an iron group metal catalyst; and (d-3) a step of producing hydroquinone by heating the DHQ or the salt thereof obtained in the step (c-3) at equal to or more than 120 degrees centigrade in the presence of a dehydration catalyst.

Each step will be described below.

1. Step (a-1): Step of producing (4S,5R,6S)-4,5,6-trihydroxy-2-cyclohexene-1-one from DOI The step (a-1) may be carried out in the same manner as in the step (a-1) described in the third embodiment.

2. Step (b-1): Step of producing THB from the (4S,5R,6S)-4,5,6-trihydroxy-2-cyclohexene-1-one The step (b-1) may be carried out in the same manner as in the step (b-1) described in the third embodiment.

3. Step (c-3): Step of producing DHQ or a salt thereof from THB

The step (c-3) may be carried out in the same manner as in the step (c-1) described in the second embodiment. After completion of the reaction, the reaction system can be replaced the inside of with inert gas and removed the metal catalyst through filtration using filter paper, celite or the like, to give the DHQ salt. Thereafter, DHQ may be prepared from the DHQ salt by neutralizing if necessary, and isolated by carrying out liquid-liquid extraction.

4. Step (d-3): Step of producing hydroquinone from the DHQ or the salt thereof.

Hydroquinone is produced from the DHQ or the salt thereof obtained in the step (c-3) using the method described in the fourth or fifth embodiment. When the catalytic reduction reaction is carried out in the presence of a basic compound in the step (c-3), the DHQ salt is obtained. Accordingly, hydroquinone can be produced by using the method described in the fifth embodiment without preparing the DHQ salt. The DHQ is isolated by desalination treatment of DHQ salt, and then hydroquinone can be produced by using the method described in the fourth embodiment. The desalting treatment of the DHQ salt may be carried out, for example, by a method of concentrating an aqueous solution of the DHQ salt after flowing it through an acidic ion exchange resin, or a method of neutralizing an aqueous solution of the DHQ salt with an acidic aqueous solution such as hydrochloric acid or the like, extracting with an organic solvent, and then concentrating the appropriate organic solvent. The purity of the DHQ obtained in the method may be increased by recrystallization or column chromatography.

In this embodiment, a solvent with low amount of dissolved oxygen may be preferably used as the reaction solvent through the steps of (a-1), (b-1), (c-3) and (d-3). Specifically, the amount of dissolved oxygen may be preferably equal to or less than 0.1 mg/L, and more preferably equal to or less than 0.02 mg/L. The similar method as the manner described in the first embodiment may be used as a method of deoxygenating a solvent.

In the method of this embodiment, each step can be efficiently carried out from DOI. Accordingly, this method is excellent as a method for producing hydroquinone industrially.

Hereinafter, effects of each step will be described in detail.

In the steps (a-1) and (b-1), in the reaction to obtain THB from DOI, the dehydration reaction is carried out in the absence of an acid catalyst using the compound represented by the above formula (1) as the reaction intermediate. Thus, the amount of the by-product generated in the presence of an acid catalyst may be reduced. Accordingly, THB can be industrially produced with using the chemical method.

As described in the first embodiment, the present inventors have made it clear that when DOI or the compound represented by the above formula (1) is subjected to a dehydration reaction in the presence of an acid catalyst, the dimer represented by the above formula (4) is obtained. The use of the obtained THB as it is for the production of hydroquinone causes a problem such that the dimer is also catalytically reduced and dehydrated to give a new by-product which is mixed into hydroquinone, thereby lowering the purity of hydroquinone.

However, in the method of this embodiment, the dehydration reaction is carried out in the absence of an acid catalyst. Thus, generation of the dimer may be prevented. Accordingly, THB can be efficiently obtained.

In the step (c-3), the catalytic hydrogenation reaction is carried out with the use of a metal catalyst containing an iron group element as a metal component. Thus, according to this method, the catalytic hydrogenation reaction is carried out with the use of an iron group metal catalyst without using a platinum group metal catalyst such as palladium, ruthenium or rhodium. The catalytic reduction reaction of hydrogen may proceed more mildly with the iron group metal, as compared to the platinum group metal. Accordingly, DHQ can be produced from THB with a good yield. Nickel or cobalt is a metal with a higher Clarke number as compared to the platinum group metal. Accordingly, such metals can be available at a low cost, and a method more suitable for industrial production may be achieved.

In the step (d-2), the same effects as those described in the fourth and fifth embodiments may be achieved.

As described above, the embodiments of the present invention have been described, but the embodiments are examples of the present invention and other various constructions can also be adopted.

EXAMPLES

Reagent

DOI was synthesized according to the method in Examples described in WO 2006/112000. A product commercially available from Wako Pure Chemical Industries, Ltd. was used as THB. A product commercially available from JGC C&C was used as 40% Ni/alumina ($Al_2O_3$). A product commercially available from JGC C&C was used as a Raney Ni. A product commercially available from Tosoh Corporation was used as sodium hydroxide. Water purified by Milli-Q Academic System commercially available from Millipore Corporation aerated with helium gas for equal to or more than 12 hours was used as water. The amount of dissolved oxygen was examined with the use of SevenGo pro commercially available from Mettler-Toledo International Inc. and as a result, the amount of dissolved oxygen was 0.02 mg/L. In Examples, the reaction was carried out in a nitrogen atmosphere unless otherwise particularly mentioned.

Analysis of DOI, (4S,5R,6S)-4,5,6-trihydroxy-2-cyclohexene-1-one, THB, DHQ, hydroquinone and dimer by HPLC Analytical Method 1

Regarding Examples A2 to A8, and Reference Examples A1 and A2, 50 µL of a sample liquid prepared with the use of a reaction solution after a period of reaction time shown in Table 1 according to the method described in each Example was injected into HPLC to detect a peak of each compound. The DOI conversion rate, the yield of (4S,5R,6S)-4,5,6-trihydroxy-2-cyclohexene-1-one, the THB yield and the dimer yield were determined from the detected peaks. The analysis conditions are shown in the following Analysis Conditions 1.

Analysis Conditions 1

Column: ODS-AQ, commercially available from YMC Co., Ltd., particle size 5 µm, inner diameter 4.6 mm×length 250 mm Eluent: 10 mM acetic acid aqueous solution/acetonitrile=97/3 (v/v)

Column temperature: 40 degrees centigrade

Analyzer: PU-2089plus, AS-2055plus, RI-2031plus, commercially available from JASCO Corporation Each retention time is as follows.

DOI: 3.3 min (4S,5R,6S)-4,5,6-trihydroxy-2-cyclohexene-1-one: 3.8 min

THB: 5.8 min

Dimer: 22.5 min

Analytical Method 2

Regarding Examples B1 to B22, B22-2, B22-3 and Reference Examples B1 to B4, 50 µL of a sample liquid prepared with the use of a reaction solution after a period of reaction time shown in each Example and each Reference Example according to the method described in each Example or Reference Example was injected into HPLC to detect a peak of each compound. The DHQ yield and the hydroquinone yield were determined from the detected peaks. In Examples B23 to B26, with the use of an analytical sample prepared according to the method described in the appropriate Example, the hydroquinone yield was determined in the same manner. The analysis conditions are shown in the following analysis conditions 2. The analysis results are shown in Tables 2 to 6. In Examples B1 to B22, B22-2, B22-3 and Reference Examples B1 to B4, each of the compounds were quantitatively analyzed according to the internal standard method with the use of 3,4-dihydroxybenzoic acid as the internal standard. Hereinafter, in Examples B1 to B22, B22-2, B22-3 and Reference Examples B1 to B4, 2.00 g (0.0100 g as an internal standard) of the following eluent solution of 0.500 weight % 3,4-dihydroxybenzoic acid prepared in advance was added thereto to give an analytical sample.

Analysis Conditions 2

Column: ODS-AQ, commercially available from YMC Co., Ltd., particle size 5 µm, inner diameter 4.6 mm×length 250 mm Eluent: 10 mM acetic acid aqueous solution/acetonitrile=97/3 (v/v)

Column temperature: 40 degrees centigrade

Analyzer: PU-2089plus, AS-2055plus, RI-2031plus, commercially available from JASCO Corporation Each retention time is as follows.

DHQ: 6.4 min

Hydroquinone: 7.9 min

Analytical Method 3

Regarding Examples C1 to C6, C12 to C16, C22 to C40, C44 to C50, C51, and Reference Examples C1, C2, C4, C5, 50 µL of a sample liquid prepared with the use of a reaction solution after a period of reaction time shown in Tables 7 to 9 according to the method described in each Example or Reference Example was injected into HPLC to detect a peak of each compound. The DHQ conversion rate and the hydroquinone yield were determined from the detected peaks. The analysis conditions are shown in the following analysis conditions 3. The analysis results are shown in Tables 7 to 9. In this analytical method 3, each of compounds were quantitatively analyzed according to the internal standard method with the use of 3,4-dihydroxybenzoic acid as the internal standard. Hereinafter, in the analytical method 3, 2.00 g (0.0100 g as an internal standard) of the following eluent solution of 0.500 weight % 3,4-dihydroxybenzoic acid prepared in advance was added thereto to give an analytical sample.

Analysis Conditions 3

Column: ODS-AQ, commercially available from YMC Co., Ltd., particle size 5 µm, inner diameter 4.6 mm×length 250 mm Eluent: 10 mM acetic acid aqueous solution/acetonitrile=97/3 (v/v)

Column temperature: 40 degrees centigrade

Analyzer: PU-2089plus, AS-2055plus, RI-2031plus, commercially available from JASCO Corporation Each retention time is as follows.

DHQ: 6.4 min

Hydroquinone: 7.9 min

Analytical Method 4

Analysis of DHQ and hydroquinone by HPLC Regarding Examples C7 to C11, C17 to C21, C41 to C43, and Reference Example C3, 10 µL of a sample liquid prepared with the use of a reaction solution after a period of reaction time shown in Tables 7 and 8 according to the method described in each Example or Reference Example was injected into HPLC to detect a peak of each compound. The DHQ conversion rate and the hydroquinone yield were determined from the detected peaks. The analysis conditions are shown in the following analysis conditions 4. The analysis results are shown in Tables 7 and 8. In this analytical method 4, each of the compounds were quantitatively analyzed according to the internal standard method with the use of 3,4-dihydroxybenzoic acid as the internal standard. Hereinafter, in the analytical method 4, 2.00 g (0.0100 g as an internal standard) of an ethanol solution of 0.500 weight % 3,4-dihydroxybenzoic acid prepared in advance was added thereto to give an analytical sample.

Analysis Conditions 4

Column: Diol-NP, commercially available from YMC Co., Ltd., inner diameter 4.6 mm×length 250 mm Eluent: 15 mM acetic acid-hexane solution/ethanol=75/25 (v/v)

Column temperature: 40 degrees centigrade

Analyzer: PU-2089plus, AS-2055plus, UV-2075plus (detection wavelength: 230 nm), commercially available from JASCO Corporation Each retention time is as follows.

DHQ: 6.4 min

Hydroquinone: 8.1 min

1. Example A

Example A corresponds to the first embodiment.

Synthesis of (4S,5R,6S)-4,5,6-trihydroxy-2-cyclohexene-1-one 1.64 g of DOI and 5 mL of a strong acid cation exchange resin (Amberlite IR120B) were added to 13.6 mL of water, and the mixture was heated under reflux for 20 hours. After completion of the reaction, an ion exchange resin was filtered, and the filtrate was concentrated under reduced pressure. The concentrated residue was purified on silica gel column (ethyl acetate), to give 604 mg (yield: 41%) of (4S,5R,6S)-4,5,6-trihydroxy-2-cyclohexene-1-one as the compound represented by the above formula (1). $^1$H-NMR data and $^{13}$C-NMR data of the compound represented by the above formula (1) are as follows.

$^1$H-NMR (CD$_3$OD; 500 MHz) data (δ ppm);
6.91 (dd, 1H, J=2.3, 11.5 Hz), 6.02 (dd, 1H, J=2.7, 11.5 Hz), 4.35 (dt, J=2.3, 8.2 Hz), 3.57 (dd, 1H, J=8.2, 11.5 Hz)
$^{13}$C-NMR (CD$_3$OD; 125 MHz) data (δ ppm);
200.18, 153.32, 127.51, 79.93, 78.12, 73.06

Example A1

1.0 g of (4S,5R,6S)-4,5,6-trihydroxy-2-cyclohexene-1-one was dissolved in 9.0 g of water, and stirred at 170 degrees centigrade for 2 hours. After completion of the reaction, the reaction solution was concentrated by removing water under reduced pressure. The residue was purified on silica gel column (hexane/ethyl acetate), to give 0.81 g (yield: 93%) of THB. $^1$H-NMR data and $^{13}$C-NMR data of THB are as follows.

$^1$H-NMR (D$_2$O; 500 MHz) data (δ ppm);
6.52 (d, 1H, J=8.7 Hz), 6.23 (d, 1H, J=2.7 Hz), 6.08 (dd, J=2.7, 8.7 Hz)
$^{13}$C-NMR (D$_2$O; 125 MHz) data (δ ppm);
6150.04, 145.44, 137.91, 114.57, 107.46, 104.51

Example A2

1.0 g of DOI was dissolved in 9.0 g of water, and stirred at 125 degrees centigrade for 10 hours in an autoclave. After completion of the reaction, the total amount of the reaction solution was recovered while it was diluted with the above-mentioned HPLC eluent, and the total amount was adjusted to be 20.0 g. 0.4 g of the diluted reaction solution and 0.01 g of 3,4-dihydroxybenzoic acid used as an internal standard were weighed, and the total amount was made up to 20 ml to give an analytical solution. The DOI conversion rate was 92%, the yield of (4S,5R,6S)-4,5,6-trihydroxy-2-cyclohexene-1-one was 27%, and the yield of 1,2,4-trihydroxybenzene was 61%.

Example A3

1.0 g of DOI was dissolved in 9.0 g of water, and stirred at 150 degrees centigrade for 8 hours in an autoclave. After completion of the reaction, the total amount of the reaction solution was recovered while it was diluted with the above-mentioned HPLC eluent, and the total amount was adjusted to be 20.0 g. 0.4 g of the diluted reaction solution and 0.01 g of 3,4-dihydroxybenzoic acid used as an internal standard were weighed, and the total amount was made up to 20 ml to give an analytical solution. The DOI conversion rate was 96%, the yield of (4S,5R,6S)-4,5,6-trihydroxy-2-cyclohexene-1-one was 0%, and the yield of 1,2,4-trihydroxybenzene was 82%.

Example A4

1.0 g of DOI was dissolved in 9.0 g of water, and stirred at 170 degrees centigrade for 2 hours in an autoclave. After completion of the reaction, the total amount of the reaction solution was recovered while it was diluted with the above-mentioned HPLC eluent, and the total amount was adjusted to be 20.0 g. 0.4 g of the diluted reaction solution and 0.01 g of 3,4-dihydroxybenzoic acid used as an internal standard were weighed, and the total amount was made up to 20 ml to give an analytical solution. The DOI conversion rate was 98%, the yield of (4S,5R,6S)-4,5,6-trihydroxy-2-cyclohexene-1-one was 4%, and the yield of 1,2,4-trihydroxybenzene was 91%.

Example A5

1.0 g of DOI was dissolved in 9.0 g of water, and stirred at 200 degrees centigrade for 2 hours in an autoclave. After completion of the reaction, the total amount of the reaction solution was recovered while it was diluted with the above-mentioned HPLC eluent, and the total amount was adjusted to be 20.0 g. 0.4 g of the diluted reaction solution and 0.01 g of 3,4-dihydroxybenzoic acid used as an internal standard were weighed, and the total amount was made up to 20 ml to give an analytical solution. The DOI conversion rate was 99%, the yield of (4S,5R,6S)-4,5,6-trihydroxy-2-cyclohexene-1-one was 0%, and the yield of 1,2,4-trihydroxybenzene was 88%.

Example A6

4.0 g of DOI was dissolved in 6.0 g of water, and stirred at 170 degrees centigrade for 2 hours in an autoclave. After completion of the reaction, the total amount of the reaction solution was recovered while it was diluted with the above-mentioned HPLC eluent, and the total amount was adjusted to be 20.0 g. 0.1 g of the diluted reaction solution and 0.01 g of 3,4-dihydroxybenzoic acid used as an internal standard were weighed, and the total amount was made up to 20 ml to give an analytical solution. The DOI conversion rate was 99%, the yield of (4S,5R,6S)-4,5,6-trihydroxy-2-cyclohexene-1-one was 0%, and the yield of 1,2,4-trihydroxybenzene was 85%.

Example A7

0.34 g of DOI was dissolved in 9.66 g of water, and stirred at 170 degrees centigrade for 2 hours in an autoclave. After completion of the reaction, the total amount of the reaction solution was recovered while it was diluted with the above-mentioned HPLC eluent, and the total amount was adjusted to be 20.0 g. 1.2 g of the diluted reaction solution and 0.01 g of 3,4-dihydroxybenzoic acid used as an internal standard were weighed, and the total amount was made up to 20 ml to give an analytical solution. The DOI conversion rate was 98%, the yield of (4S,5R,6S)-4,5,6-trihydroxy-2-cyclohexene-1-one was 0%, and the yield of 1,2,4-trihydroxybenzene was 91%.

Example A8

0.1 g of DOI was dissolved in 9.9 g of water, and stirred at 170 degrees centigrade for 2 hours in an autoclave. After completion of the reaction, the total amount of the reaction solution was recovered while it was diluted with the above-mentioned HPLC eluent, and the total amount was adjusted to be 20.0 g. 4 g of the diluted reaction solution and 0.01 g of 3,4-dihydroxybenzoic acid used as an internal standard were weighed, and the total amount was made up to 20 ml to give an analytical solution. The DOI conversion rate was 100%, the yield of (4S,5R,6S)-4,5,6-trihydroxy-2-cyclohexene-1-one was 3%, and the yield of 1,2,4-trihydroxybenzene was 95%.

Reference Example A1

1.0 g of DOI was dissolved in 9.0 g of water and 0.08 g (0.14 equivalents relative to DOI) of phosphoric acid was further added thereto, and the mixture was stirred at 170 degrees centigrade for 2 hours in an autoclave. After completion of the reaction, the total amount of the reaction solution was recovered while it was diluted with the above-mentioned HPLC eluent, and the total amount was adjusted to be 20.0 g. 0.4 g of the diluted reaction solution and 0.01 g of 3,4-dihydroxybenzoic acid used as an internal standard were weighed, and the total amount was made up to 20 ml to give an analytical solution. The DOI conversion rate was 98%, the yield of (4S,5R,6S)-4,5,6-trihydroxy-2-cyclohexene-1-one was 0%, the yield of 1,2,4-trihydroxybenzene was 81%, and the dimer yield was 19%.

Reference Example A2

1.0 g of DOI was dissolved in 9.0 g of water and 0.002 g ($0.36 \times 10^{-2}$ equivalents relative to DOI) of sulfuric acid was further added thereto, and the mixture was stirred at 170 degrees centigrade for 2 hours in an autoclave. After completion of the reaction, the total amount of the reaction solution was recovered while it was diluted with the above-mentioned HPLC eluent, and the total amount was adjusted to be 20.0 g. 0.4 g of the diluted reaction solution and 0.01 g of 3,4-dihydroxybenzoic acid used as an internal standard were weighed, and the total amount was made up to 20 ml to give an analytical solution. The DOI conversion rate was 100%, the yield of (4S,5R,6S)-4,5,6-trihydroxy-2-cyclohexene-1-one was 14%, the yield of 1,2,4-trihydroxybenzene was 72%, and the dimer yield was 14%.

The results of Examples A2 to A8 and Reference Examples A1 and A2 are shown in Table 1.

TABLE 1

| | Acid catalyst | Reaction temperature (° C.) | Reaction time (hour) | Concentration (weight %) | THB yield (%) | Dimer yield (%) |
| --- | --- | --- | --- | --- | --- | --- |
| Example A2 | No | 125 | 10 | 10 | 61 | 0 |
| Example A3 | No | 150 | 8 | 10 | 82 | 0 |
| Example A4 | No | 170 | 2 | 10 | 91 | 0 |
| Example A5 | No | 200 | 2 | 10 | 88 | 0 |
| Example A6 | No | 170 | 2 | 40 | 85 | 0 |
| Example A7 | No | 170 | 2 | 3.4 | 91 | 0 |
| Example A8 | No | 170 | 2 | 1 | 95 | 0 |
| Reference Example A1 | Phosphoric acid | 170 | 2 | 10 | 81 | 19 |
| Reference Example A2 | Sulfuric acid | 170 | 2 | 10 | 72 | 14 |

2. Example B

Example B corresponds to the second and third embodiments.

In each of Examples B1 to B9, the step (c-1) described in the second embodiment was carried out.

Example B1

284 mg (2.25 mmol) of THB, 35.9 mg of 40% Ni/alumina and 89.9 mg (2.25 mmol) of sodium hydroxide were put into a 70-ml autoclave, and the system was replaced with nitrogen of 0.5 MPa three times. Thereafter, 13.9 g of water was added thereto under a nitrogen stream. Furthermore, the atmosphere inside the reaction system was replaced with hydrogen of 0.5 MPa three times, and then the hydrogen pressure inside the reactor was set to 0.23 MPa. The inside of the reactor was heated with stirring and the internal temperature was adjusted to be 100 degrees centigrade. This internal temperature was taken as the reaction temperature. After the reaction was carried out for 3.5 hours, the reactor was cooled until the temperature inside the reactor became near room temperature (25 degrees centigrade). Under a nitrogen stream, an insoluble matter was removed from the total amount of the reaction solution using filter paper having a micro-pore diameter of 1 μm. The residue was washed with water, and then diluted with water such that the total amount became 40.0 g. The above-mentioned internal standard solution was added to 2.82 g of the liquid diluent, and the total amount was made up to 20 ml to give an analytical solution.

Example B2

An operation was carried out in the same manner as in Example B1, except that 14.2 mg of Raney Ni was used instead of 40% Ni/alumina.

Example B3

An operation was carried out in the same manner as in Example B1, except that the reaction temperature was changed to 125 degrees centigrade.

Example B4

An operation was carried out in the same manner as in Example B1, except that the reaction temperature was changed to 75 degrees centigrade.

Example B5

An operation was carried out in the same manner as in Example B1, except that the reaction temperature was changed to 50 degrees centigrade and the reaction time was changed to 14 hours.

Example B6

An operation was carried out in the same manner as in Example B1, except that the reaction temperature was changed to 25 degrees centigrade and the reaction time was changed to 76 hours.

Example B7

3.33 g (26.4 mmol) of THB, 427 mg of 40% Ni/alumina and 1.06 g (26.4 mmol) of sodium hydroxide were put into a 100-ml autoclave, and the system was replaced with nitrogen of 0.5 MPa three times. Thereafter, 30.0 g of water was added thereto under a nitrogen stream. Furthermore, the atmosphere inside the reaction system was replaced with hydrogen of 0.5 MPa three times, and then the hydrogen pressure inside the reactor was set to 2.5 MPa. The inside of the reactor was heated with stirring and the internal temperature was adjusted to be 50 degrees centigrade. After the reaction was carried out for 5 hours, the reactor was cooled until the temperature inside the reactor became near room temperature (25 degrees centigrade). Under a nitrogen stream, an insoluble matter was removed from the total amount of the reaction solution using filter paper having a micro-pore diameter of 1 μm. The residue was washed with water, and then diluted with water such that the total amount became 60.0 g. The above-mentioned internal standard solution was added to 0.360 g of the liquid diluent, and the total amount was made up to 20 ml to give an analytical solution.

Example B8

7.50 g (59.5 mmol) of THB, 427 mg of 40% Ni/alumina and 2.38 g (59.5 mmol) of sodium hydroxide were put into a 100-ml autoclave, and the system was replaced with nitrogen of 0.5 MPa three times. Thereafter, 30.0 g of water was added thereto under a nitrogen stream. Furthermore, the atmosphere inside the reaction system was replaced with hydrogen of 0.5 MPa three times, and then the hydrogen pressure inside the reactor was set to 10 MPa. The inside of the reactor was heated with stirring and the internal temperature was adjusted to be 50 degrees centigrade. After the reaction was carried out for 5 hours, the reactor was cooled until the temperature inside the reactor became near room temperature (25 degrees centigrade). Under a nitrogen stream, an insoluble matter was removed from the total amount of the reaction solution using filter paper having a micro-pore diameter of 1 μm. The residue was washed with water, and then diluted with water such that the total amount became 60.0 g. The above-mentioned internal standard solution was added to 0.160 g of the liquid diluent, and the total amount was made up to 20 ml to give an analytical solution.

Example B9

12.9 g (102 mmol) of THB, 427 mg of 40% Ni/alumina and 4.09 g (102 mmol) of sodium hydroxide were put into a 100-ml autoclave, and the system was replaced with nitrogen of 0.5 MPa three times. Thereafter, 30.0 g of water was added thereto under a nitrogen stream. Furthermore, the atmosphere inside the reaction system was replaced with hydrogen of 0.5 MPa three times, and then the hydrogen pressure inside the reactor was set to 10 MPa. The inside of the reactor was heated with stirring and the internal temperature was adjusted to be 50 degrees centigrade. After the reaction was carried out for 12 hours, the reactor was cooled until the temperature inside the reactor became near room temperature (25 degrees centigrade). Under a nitrogen stream, an insoluble matter was removed from the total amount of the reaction solution using filter paper having a micro-pore diameter of 1 μm. The residue was washed with water, and then diluted with water such that the total amount became 100.0 g. The above-mentioned internal standard solution was added to 0.150 g of the liquid diluent, and the total amount was made up to 20 ml to give an analytical solution.

The results of Examples B1 to B9 are shown in Table 2. Incidentally, the concentration is represented by [{weight of THB/(weight of THB+weight of water)}×100].

TABLE 2

| | Catalyst | | | | | | |
|---|---|---|---|---|---|---|---|
| | Type | Metal/THB (weight %) | Catalyst/THB (weight %) | Reaction temperature (° C.) | Reaction time | Concentration (weight %) | DHQ yield (%) |
| Example B1 | Ni/Al$_2$O$_3$ | 5 | 12.6 | 100 | 3.5 | 2 | 88 |
| Example B2 | Raney Ni | 5 | 5 | 100 | 3.5 | 2 | 71 |
| Example B3 | Ni/Al$_2$O$_3$ | 5 | 12.6 | 125 | 3.5 | 2 | 69 |
| Example B4 | Ni/Al$_2$O$_3$ | 5 | 12.6 | 75 | 3.5 | 2 | 97 |
| Example B5 | Ni/Al$_2$O$_3$ | 5 | 12.6 | 50 | 14 | 2 | 100 |
| Example B6 | Ni/Al$_2$O$_3$ | 5 | 12.6 | 25 | 76 | 2 | 100 |
| Example B7 | Ni/Al$_2$O$_3$ | 5 | 12.8 | 50 | 5 | 10 | 96 |
| Example B8 | Ni/Al$_2$O$_3$ | 2.3 | 5.7 | 50 | 5 | 20 | 99 |
| Example B9 | Ni/Al$_2$O$_3$ | 1.3 | 3.3 | 50 | 12 | 30 | 88 |

In each of Examples B10 to B13, the steps (c-1) and (d-1) described in the second embodiment were carried out.

Example B10

3.33 g (26.4 mmol) of THB, 427 mg of 40% Ni/alumina and 1.06 g (26.4 mmol) of sodium hydroxide were put into a 100-ml autoclave, and the system was replaced with nitrogen of 0.5 MPa three times. Thereafter, 30.0 g of water was added thereto under a nitrogen stream. Furthermore, the atmosphere inside the reaction system was replaced with hydrogen of 0.5 MPa three times, and then the hydrogen pressure inside the reactor was set to 2.5 MPa. The inside of the reactor was heated with stirring and the internal temperature was adjusted to be 50 degrees centigrade. After the reaction was carried out for 5 hours, the reactor was cooled until the temperature inside the reactor became near room temperature (25 degrees centigrade). Under a nitrogen stream, an insoluble matter was removed from the total amount of the reaction solution using filter paper having a micro-pore diameter of 1 μm. The filtrate was allowed to pass through a column filled with 50 ml of Diaion PK212LH (a product of Mitsubishi Chemical Corporation) which was separately prepared at a speed of SV=3, and 200 ml of pure water was further allowed to pass through the column. The total amount of the liquid passing through the column was collected and concentrated at a temperature not exceeding 50 degrees centigrade to obtain 3.22 g of DHQ (yield: 95%).

$^1$H-NMR (CD$_3$OD; 500 MHz) data (δ ppm) of DHQ; 1.83 (m, 1H), 2.20 (m, 1H), 2.48 (m, 2H), 4.10 (dd, 1H, J=5.0, 11.3 Hz), 5.31 (s, 1H)

$^{13}$C-NMR (D$_2$O; 125 MHz) data (δ ppm) of DHQ; 196.43, 187.91, 102.31, 69.52, 29.29, 29.22

Next, 1.00 g (7.80 mmol) of DHQ obtained as described above and 0.312 g (7.80 mmol) of sodium hydroxide were dissolved in 9.00 g of water to give an aqueous sodium salt solution of DHQ. The aqueous solution and 1.00 g (100 weight %) of hydroquinone were put into a 70-ml autoclave. The system was heated until the internal temperature became 200 degrees centigrade, and the reaction was carried out at that temperature for 30 minutes. The reactor was cooled until the temperature became near room temperature (25 degrees centigrade), and then the reaction solution was recovered while water was added thereto, thereby making the total amount 100.0 g. The above-mentioned internal standard solution was added to 1.00 g of the liquid diluent, and the total amount was made up to 20 ml to give an analytical solution.

Example B11

An operation was carried out in the same manner as in Example B10, except that 2.00 g (200 weight %) of hydroquinone was used, and the amount of the liquid diluent used for analysis was changed to 0.670 g.

Example B12

An operation was carried out in the same manner as in Example B10, except that 3.00 g (300 weight %) of hydroquinone was used, and the amount of the liquid diluent used for analysis was changed to 0.500 g.

Example B13

An operation was carried out in the same manner as in Example B10, except that 4.00 g (400 weight %) of hydroquinone was used, and the amount of the liquid diluent used for analysis was changed to 0.400 g.

The results of Examples B10 to B13 are shown in Table 3.

TABLE 3

| | Amount of hydroquinone added (weight %) | Hydroquinone yield (%) |
| --- | --- | --- |
| Example B10 | 100 | 59 |
| Example B11 | 200 | 61 |
| Example B12 | 300 | 75 |
| Example B13 | 400 | 84 |

Example B14

An operation was carried out in the same manner as in Example B10, except that 1.00 g (100 weight %) of catechol was used instead of hydroquinone, and the amount of the liquid diluent used for analysis was changed to 2.00 g.

Example B15

An operation was carried out in the same manner as in Example B10, except that 1.00 g (100 weight %) of resorcinol was used instead of hydroquinone, and the amount of the liquid diluent used for analysis was changed to 2.00 g.

Example B16

An operation was carried out in the same manner as in Example B10, except that 1.00 g (100 weight %) of 1,2,3-trihydroxybenzene was used instead of hydroquinone, and the amount of the liquid diluent used for analysis was changed to 2.00 g.

Example B17

An operation was carried out in the same manner as in Example B10, except that 1.00 g (100 weight %) of 1,3,5-trihydroxybenzene was used instead of hydroquinone, and the amount of the liquid diluent used for analysis was changed to 2.00 g.

Example B18

An operation was carried out in the same manner as in Example B10, except that 1.00 g (100 weight %) of phenol was used instead of hydroquinone, and the amount of the liquid diluent used for analysis was changed to 2.00 g.

Example B19

An operation was carried out in the same manner as in Example B10, except that 4.00 g (400 weight %) of catechol was used instead of hydroquinone, the reaction temperature was changed to 180 degrees centigrade, and the amount of the liquid diluent used for analysis was changed to 2.00 g.

Example B20

An operation was carried out in the same manner as in Example B10, except that 4.00 g (400 weight %) of resorcinol was used instead of hydroquinone, the reaction temperature was changed to 180 degrees centigrade, and the amount of the liquid diluent used for analysis was changed to 2.00 g.

Example B21

An operation was carried out in the same manner as in Example B10, except that 4.00 g (400 weight %) of THB was used instead of hydroquinone, and the amount of the liquid diluent used for analysis was changed to 2.00 g.

The results of Examples B14 to B21 are shown in Table 4.

TABLE 4

| | Additive | Additive (weight %) | Reaction temperature (° C.) | Hydroquinone yield (%) |
| --- | --- | --- | --- | --- |
| Example B14 | Catechol | 100 | 200 | 73 |
| Example B15 | Resorcinol | 100 | 200 | 67 |
| Example B16 | 1,2,3-tri-hydroxy-benzene | 100 | 200 | 83 |
| Example B17 | 1,3,5-tri-hydroxy-benzene | 100 | 200 | 64 |
| Example B18 | Phenol | 100 | 200 | 57 |
| Example B19 | Catechol | 400 | 180 | 85 |
| Example B20 | Resorcinol | 400 | 180 | 82 |
| Example B21 | THB | 400 | 200 | 78 |

Reference Example B1

An operation was carried out in the same manner as in Example B10, except that 0.312 g of sodium hydroxide was not used.

Reference Example B2

An operation was carried out in the same manner as in Example B10, except that 0.312 g of sodium hydroxide was not used, 1.00 g (100 weight %) of catechol was used instead of hydroquinone, and the amount of the liquid diluent used for analysis was changed to 2.00 g.

Reference Example B3

An operation was carried out in the same manner as in Example B10, except that 0.312 g of sodium hydroxide was not used, 1.00 g (100 weight %) of resorcinol was used instead of hydroquinone, and the amount of the liquid diluent used for analysis was changed to 2.00 g.

Reference Example B4

An operation was carried out in the same manner as in Example B10, except that 0.312 g of sodium hydroxide was not used, 1.00 g (100 weight %) of phenol was used instead of hydroquinone, and the amount of the liquid diluent used for analysis was changed to 2.00 g.

The results of Reference Examples B1 to B4 are shown in Table 5.

TABLE 5

| | Additive | Hydroquinone yield (%) |
|---|---|---|
| Reference Example B1 | Hydroquinone | 14 |
| Reference Example B2 | Catechol | 14 |
| Reference Example B3 | Resorcinol | 13 |
| Reference Example B4 | Phenol | 37 |

Example B22

10.0 g (61.7 mmol) of DOI was dissolved in 9.0 g of water, and stirred at 170 degrees centigrade for 2 hours in a 200-ml autoclave. The system was cooled down to room temperature (25 degrees centigrade) (a reaction solution A). Separately, 0.91 g of 40% Ni/alumina and 2.25 g (56.1 mmol) of sodium hydroxide were put into a 200-ml autoclave, and the system was replaced with nitrogen of 0.5 MPa three times. The total amount of the aforementioned reaction solution A was put into this reactor under a nitrogen stream. The atmosphere inside the reactor was replaced with hydrogen of 0.5 MPa three times, and then the hydrogen pressure inside the reactor was set to 2.5 MPa. The inside of the reactor was heated with stirring and the internal temperature was adjusted to be 50 degrees centigrade. After the reaction was carried out for 14 hours, the reactor was cooled until the temperature inside the reactor became near room temperature. Next, an insoluble matter was filtered (a filtrate B) using filter paper having a micro-pore diameter of 1 μm. 27.9 g (253 mmol) of hydroquinone was added to the filtrate B, and put into the 200-ml autoclave again under a nitrogen stream. The reactor was heated until the internal temperature became 200 degrees centigrade, the reaction was carried out at that temperature for 0.5 hours, and then the reactor was cooled down to near room temperature (25 degrees centigrade) (a reaction solution B). The reaction solution B was recovered while it was diluted with the above-mentioned HPLC eluent such that the total amount became 330 g. The above-mentioned internal standard solution was added to 0.200 g of the recovery solution, and the total amount was made up to 20 ml to give an analytical solution. The quantitative analysis was carried out using the analysis conditions described in the aforementioned analytical method and as a result, 32.8 g of hydroquinone was detected. It was found that 4.92 g (44.6 mmol) of hydroquinone was increased as compared to the added amount, and hydroquinone was produced from DOI at a yield of 72%.

Example B22-2

10.0 g (61.7 mmol) of DOI was dissolved in 90.0 g of water, and stirred at 170 degrees centigrade for 2 hours in a 200-ml autoclave. The system was cooled down to room temperature (25 degrees centigrade) (a reaction solution A2). Separately, 0.91 g of 40% Ni/alumina and 2.25 g (56.1 mmol) of sodium hydroxide were put into a 200-ml autoclave, and the system was replaced with nitrogen of 0.5 MPa three times. The total amount of the aforementioned reaction solution A2 was put into this reactor under a nitrogen stream. The atmosphere inside the reactor was replaced with hydrogen of 0.5 MPa three times, and then the hydrogen pressure inside the reactor was set to 2.5 MPa. The inside of the reactor was heated with stirring and the internal temperature was adjusted to be 50 degrees centigrade. After the reaction was carried out for 14 hours, the reactor was cooled until the temperature inside the reactor became near room temperature. Next, an insoluble matter was filtered (a filtrate B2) using filter paper having a micro-pore diameter of 1 pm. 27.9 g (253 mmol) of hydroquinone was added to the filtrate B2, and put into the 200-ml autoclave again under a nitrogen stream. The reactor was heated until the internal temperature became 180 degrees centigrade, the reaction was carried out at that temperature for 0.5 hours, and then the reactor was cooled down to near room temperature (25 degrees centigrade) (a reaction solution B2). Since a large amount of white solid was precipitated in the reaction solution B2, this white solid was separated through filtration by nitrogen gas pressurization, and the white solid was further washed with 10 g of cold pure water. The obtained white solid was 30.3 g. The above-mentioned internal standard solution was added to 0.0300 g of the white solid, and the total amount was made up to 20 ml to give an analytical solution. The purity of hydroquinone in the white solid was 67.3%, and 20.4 g of hydroquinone was contained in the solid. According to HPLC analysis, peaks of other than hydroquinone and the internal standard were not observed. The weight component other than hydroquinone is considered to be water.

Example B22-3

5.0 g (30.8 mmol) of DOI was dissolved in 45.0 g of water, and stirred at 170 degrees centigrade for 2 hours in a 100-ml autoclave. The system was cooled down to room temperature (25 degrees centigrade) (a reaction solution A3). Aside from this, 0.45 g of 40% Ni/alumina and 1.13 g (28.1 mmol) of sodium hydroxide were put into a 100-ml autoclave, and the system was replaced with nitrogen of 0.5 MPa three times. The total amount of the aforementioned reaction solution A3 was put into this reactor under a nitrogen stream. The atmosphere inside the reactor was replaced with hydrogen of 0.5 MPa three times, and then the hydrogen pressure inside the reactor was set to 2.5 MPa. The inside of the reactor was heated with stirring and the internal temperature was adjusted to be 50 degrees centigrade. After the reaction was carried out for 14 hours, the reactor was cooled until the temperature inside the reactor became near room temperature. Next, an insoluble matter was filtered (a filtrate B3) using filter paper having a micro-pore diameter of 1 μm. 25.0 g (16.8 g (153 mmol) as hydroquinone) of the white solid obtained in Example B22-2 was added to the filtrate B3, and put into the 100-ml autoclave again under a nitrogen stream. The reactor was heated until the internal temperature became 180 degrees centigrade, the reaction was carried out at that temperature for 0.5 hours, and then the reactor was cooled down to near room temperature (25 degrees centigrade) (a reaction solution B3). The reaction solution B3 was recovered while it was diluted with the above-mentioned HPLC eluent, such that the total amount became 200 g. The above-mentioned internal standard solution was added to 0.200 g of the recovery solution, and the total amount was made up to 20 ml to give an analytical solution. The quantitative analysis was carried out using the analysis conditions described in the aforementioned analytical method, thereby detecting 19.1 g of hydroquinone. It was found that 2.33 g (21.2 mmol) of hydroquinone as compared to the added amount, and hydroquinone was produced from DOI at a yield of 69%.

Example B23

1.00 g (7.80 mmol) of DHQ obtained in the same manner as the method described in the first half of Example B10 and 0.312 g (7.80 mmol) of sodium hydroxide were dissolved in 9.00 g of water to give an aqueous sodium salt solution of DHQ. The aqueous solution and 4.00 g (400 weight %) of hydroquinone were put into a 70-ml autoclave. The system was heated until the internal temperature became 180 degrees centigrade, and the reaction was carried out at that temperature for 30 minutes. The reactor was cooled down to near room temperature (25 degrees centigrade), and then 7.80 ml (15.6 mmol as $H^+$) of an aqueous solution of 1.0M sulfuric acid was added thereto in a nitrogen atmosphere. The contents were immediately moved to a 200-ml separatory funnel, and the contents were recovered while the inside of the autoclave was further washed with pure water. The aqueous solution became approximately 40 ml. Next, 80 ml of methyl isobutyl ketone (MIBK) was added to the separatory funnel to carry out extraction. Extraction was further carried out twice using the same amount of MIBK, and the collected organic layer was removed using a rotary evaporator. The residue was dried under reduced pressure (1 mmHg) at room temperature and as a result, 4.85 g of solid was obtained. 0.100 g of the solid and 0.100 g 3,4-dihydroxybenzoic acid used as an internal standard were weighed, and an analytical solution was diluted with the above-mentioned HPLC eluent so as to adjust the total amount to 100 ml. The analytical solution was analyzed under the analysis conditions described in the aforementioned analytical method 2, and hydroquinone was quantitatively analyzed, thereby found to contain 4.76 g of hydroquinone. Incidentally, DHQ was not observed at all and the raw material was completely disappeared.

Furthermore, an aqueous layer in the aforementioned extraction procedure was analyzed. The total amount of the recovered aqueous layer was 40.5 g. 0.100 g of 3,4-dihydroxybenzoic acid as an internal standard weighed in advance was added to the total amount of the aqueous layer, and the analytical solution was further diluted with the above-mentioned HPLC eluent so as to adjust the total amount to 100 ml. This analytical solution was analyzed under the analysis conditions described in the aforementioned analytical method 2, and hydroquinone was quantitatively analyzed thereby found to contain 0.0143 g of hydroquinone. 4.77 g of hydroquinone in total was observed by combining hydroquinone analyzed with the organic layer and hydroquinone analyzed with the aqueous layer. It was estimated from the fact that hydroquinone added at the start of the reaction was 4.00 g that 0.77 g (7.03 mmol) of hydroquinone was produced from 1.00 g (7.80 mmol) of DHQ in this reaction, therefore it found that the hydroquinone yield was 90.1%.

Example B24

An operation was carried out in the same manner as in Example B23, except that the reaction temperature was changed to 140 degrees centigrade, and the reaction time was changed to 4 hours.

Example B25

An operation was carried out in the same manner as in Example B23, except that the reaction temperature was changed to 150 degrees centigrade, and the reaction time was changed to 2 hours.

Example B26

An operation was carried out in the same manner as in Example B23, except that the reaction temperature was changed to 160 degrees centigrade, and the reaction time was changed to 1 hour.

The results of Examples B23 to B26 are shown in Table 6.

TABLE 6

|  | Reaction temperature (° C.) | Reaction time (hour) | Hydroquinone yield (%) |
| --- | --- | --- | --- |
| Example B23 | 180 | 0.5 | 90 |
| Example B24 | 140 | 4.0 | 87 |
| Example B25 | 150 | 2.0 | 90 |
| Example B26 | 160 | 1.0 | 90 |

3. Example C

Example C corresponds to the fourth to sixth embodiments.

In Example C, DHQ was prepared in the same manner as in Example B10.

Example C1

1.00 g of DHQ prepared as described above was dissolved in 14.6 g of water to prepare a DHQ solution having a concentration of 6.41 weight %. Subsequently, 1.53 g (2 moles relative to DHQ) of sulfuric acid was added thereto, and the mixture was heated in a glass autoclave to carry out the dehydration reaction. The reaction temperature was 120 degrees centigrade, and the reaction time was 4 hours. After completion of the reaction, the total amount of the reaction solution was recovered while it was diluted with the eluent described in the aforementioned analytical method 3, and the total amount was adjusted to be 20.0 g. The above-mentioned internal standard solution was added to 0.400 g of the diluted reaction solution, and the total amount was made up to 20 ml to give an analytical solution.

Example C2

An operation was carried out in the same manner as in Example C1, except that the reaction temperature was changed to 170 degrees centigrade.

Example C3

0.500 g of DHQ prepared as described above was dissolved in 24.5 g of water to prepare a DHQ solution having a concentration of 2.00 weight %. Subsequently, 0.770 g (2 moles relative to DHQ) of sulfuric acid was added thereto, and the mixture was heated in a glass autoclave to carry out the dehydration reaction. The reaction temperature was 120 degrees centigrade, and the reaction time was 8 hours. After completion of the reaction, the total amount of the reaction solution was recovered while it was diluted with the eluent described in the aforementioned analytical method 3, and the total amount was adjusted to be 40.0 g. The above-mentioned internal standard solution was added to 1.60 g of the diluted reaction solution, and the total amount was made up to 20 ml to give an analytical solution.

Example C4

An operation was carried out in the same manner as in Example C3, except that the reaction temperature was changed to 180 degrees centigrade.

Example C5

An operation was carried out in the same manner as in Example C3, except that the reaction temperature was changed to 200 degrees centigrade.

Example C6

0.200 g of DHQ prepared as described above was dissolved in 19.8 g of water to prepare a DHQ solution having a concentration of 1.00 weight %. Subsequently, 0.600 g of zeolite Hβ (serial No.: BEA-12.5ALY-98527, commercially available from N.E. Chemcat Corporation) was added thereto, and the mixture was heated in an autoclave to carry out the dehydration reaction. The reaction temperature was 210 degrees centigrade, and the reaction time was 1 hour. After completion of the reaction, an insoluble matter was filtered using filter paper having a micro-pore diameter of 0.2 μm, and the residue was washed with the eluent described in the aforementioned analytical method 3. It was diluted such that the total amount became 40.0 g. Then, the above-mentioned internal standard solution was added to 4.00 g of the liquid diluent, and the total amount was made up to 20 ml to give an analytical solution.

Example C7

0.500 g of DHQ prepared as described above was dissolved in 24.5 g of acetonitrile to prepare a DHQ solution having a concentration of 2.00 weight %. Subsequently, 1.50 g of zeolite Hβ (serial No.: BEA-12.5ALY-98527, commercially available from N.E. Chemcat Corporation) was added thereto, and the mixture was heated in an autoclave to carry out the dehydration reaction. The reaction temperature was 180 degrees centigrade, and the reaction time was 1 hour. After completion of the reaction, an insoluble matter was filtered using filter paper having a micro-pore diameter of 0.2 μm, and the residue was washed with ethanol. It was diluted with ethanol such that the total amount became 40.0 g. Then, the above-mentioned internal standard solution was added to 1.60 g of the liquid diluent, and the total amount was made up to 20 ml to give an analytical solution.

Example C8

An operation was carried out in the same manner as in Example C7, except that 24.5 g of propionitrile was used instead of acetonitrile, and the reaction temperature was changed to 200 degrees centigrade.

Example C9

An operation was carried out in the same manner as in Example C7, except that 24.5 g of benzonitrile was used instead of acetonitrile.

Example C10

An operation was carried out in the same manner as in Example C7, except that 24.5 g of dioxane was used instead of acetonitrile.

Example C11

An operation was carried out in the same manner as in Example C7, except that 24.5 g of methyl isobutyl ketone (MIBK) was used instead of acetonitrile.

Example C12

1.00 g of DHQ prepared as described above was dissolved in 9.00 g of water to prepare a DHQ solution having a concentration of 10.0 weight %. Subsequently, 3.00 g of zeolite Hβ (serial No.: BEA-12.5ALY-98527, commercially available from N.E. Chemcat Corporation) was added thereto, and the mixture was heated in an autoclave to carry out the dehydration reaction. The reaction temperature was 200 degrees centigrade, and the reaction time was 0.5 hours. After completion of the reaction, an insoluble matter was filtered using filter paper having a micro-pore diameter of 0.2 μm, and the residue was washed with the eluent described in the aforementioned analytical method 3. It was diluted such that the total amount became 20.0 g. Then, the above-mentioned internal standard solution was added to 0.400 g of the diluted reaction solution, and the total amount was made up to 20 ml to give an analytical solution.

Example C13

An operation was carried out in the same manner as in Example C13, except that the amount of zeolite Hβ added was changed to 1.00 g.

Example C14

0.500 g of DHQ prepared as described above was dissolved in 24.5 g of water to prepare a DHQ solution having a concentration of 2.00 weight %. Subsequently, 0.100 g of zeolite Hβ (serial No.: BEA-12.5ALY-98527, commercially available from N.E. Chemcat Corporation) was added thereto, and the mixture was heated in an autoclave to carry out the dehydration reaction. The reaction temperature was 200 degrees centigrade, and the reaction time was 8 hours. After completion of the reaction, an insoluble matter was filtered using filter paper having a micro-pore diameter of 0.2 μm, and the residue was washed with the eluent described in the aforementioned analytical method 3. It was diluted such that the total amount became 40.0 g. Then, the above-mentioned internal standard solution was added to 1.60 g of the diluted reaction solution, and the total amount was made up to 20 ml to give an analytical solution.

Example C15

An operation was carried out in the same manner as in Example C14, except that 0.100 g of zeolite H-USY (model number: HSZ-360HUA, commercially available from Tosoh Corporation, SiO$_2$/Al$_2$O$_3$=13.9) was used instead of zeolite Hβ.

Example C16

An operation was carried out in the same manner as in Example C6, except that 0.600 g of alumina (Al$_2$O$_3$, product number: 199966, commercially available from Sigma-Aldrich Japan) was used instead of zeolite Hβ, and the reaction temperature was changed to 200 degrees centigrade.

Example C17

An operation was carried out in the same manner as in Example C7, except that 1.50 g of alumina (Al$_2$O$_3$, Product number: 199966, commercially available from Sigma-Aldrich Japan) was used instead of zeolite Hβ, and the reaction temperature was changed to 220 degrees centigrade.

Example C18

An operation was carried out in the same manner as in Example C7, except that 24.5 g of propionitrile was used instead of acetonitrile, 1.50 g of alumina (Al$_2$O$_3$, product number: 199966, commercially available from Sigma-Aldrich Japan) was used instead of zeolite Hβ, and the reaction temperature was changed to 220 degrees centigrade.

Example C19

An operation was carried out in the same manner as in Example C7, except that 24.5 g of benzonitrile was used instead of acetonitrile, 1.50 g of alumina (Al$_2$O$_3$, product number: 199966, commercially available from Sigma-Aldrich Japan) was used instead of zeolite Hβ, and the reaction temperature was changed to 220 degrees centigrade.

Example C20

An operation was carried out in the same manner as in Example C7, except that 24.5 g of methyl isobutyl ketone (MIBK) was used instead of acetonitrile, and 1.50 g of alumina (Al$_2$O$_3$, product number: 199966, commercially available from Sigma-Aldrich Japan) was used instead of zeolite Hβ.

Example C21

1.00 g of DHQ prepared as described above was dissolved in 9.00 g of 2-butanol to prepare a DHQ solution having a concentration of 10.0 weight %. Subsequently, 3.00 g of alumina (Al$_2$O$_3$, product number: 199966, commercially available from Sigma-Aldrich Japan) was added thereto, and the mixture was heated in an autoclave to carry out the dehydration reaction. The reaction temperature was 200 degrees centigrade, and the reaction time was 0.5 hours. After completion of the reaction, an insoluble matter was filtered using filter paper having a micro-pore diameter of 0.2 μm, and the residue was washed with ethanol. It was diluted with ethanol such that the total amount became 20.0 g. Then, the above-mentioned internal standard solution was added to 0.400 g of the diluted reaction solution, and the total amount was made up to 20 ml to give an analytical solution.

Example C22

An operation was carried out in the same manner as in Example C14, except that 0.100 g of alumina MSU-X (a product of Sigma-Aldrich Japan) was used instead of zeolite Hβ.

Example C23

An operation was carried out in the same manner as in Example C6, except that 0.600 g of alumina MSU-X (a product of Sigma-Aldrich Japan) was used instead of zeolite Hβ, the reaction temperature was changed to 200 degrees centigrade, and the reaction time was changed to 0.5 hours.

Example C24

An operation was carried out in the same manner as in Example C6, except that 0.600 g of activated clay (a product of Wako Pure Chemical Industries, Ltd.) was used instead of zeolite Hβ, the reaction temperature was changed to 200 degrees centigrade, and the reaction time was changed to 0.5 hours.

Example C25

An operation was carried out in the same manner as in Example C6, except that 0.600 g of montmorillonite K10 (a product of Sigma-Aldrich Japan) was used instead of zeolite Hβ, the reaction temperature was changed to 200 degrees centigrade, and the reaction time was changed to 0.5 hours.

Example C26

An operation was carried out in the same manner as in Example C14, except that 0.500 g of magnesium oxide (MgO) was used instead of zeolite Hβ.

Example C27

1.00 g of DHQ prepared as described above was dissolved in 9.00 g of water to prepare a DHQ solution having a concentration of 10 weight %. Subsequently, 3.00 g of lithium acetate was added thereto, and the mixture was heated in an autoclave to carry out the dehydration reaction. The reaction temperature was 200 degrees centigrade, and the reaction time was 0.5 hours. After completion of the reaction, the total amount of the reaction solution was recovered while it was diluted with the eluent described in the aforementioned analytical method 3, and the total amount was adjusted to be 20.0 g. The above-mentioned internal standard solution was added to 0.400 g of the diluted reaction solution, and the total amount was made up to 20 ml to give an analytical solution.

Example C28

An operation was carried out in the same manner as in Example C27, except that 1.00 g of sodium acetate was used instead of lithium acetate.

Example C29

An operation was carried out in the same manner as in Example C27, except that 3.00 g of sodium acetate was used instead of lithium acetate.

Example C30

An operation was carried out in the same manner as in Example C27, except that 3.00 g of potassium acetate was used instead of lithium acetate, and the reaction temperature was changed to 180 degrees centigrade.

Example C31

An operation was carried out in the same manner as in Example C27, except that 3.00 g of potassium acetate was used instead of lithium acetate.

Example C32

An operation was carried out in the same manner as in Example C27, except that 3.00 g of rubidium acetate was used instead of lithium acetate.

Example C33

An operation was carried out in the same manner as in Example C27, except that 3.00 g of cesium acetate was used instead of lithium acetate.

Example C34

An operation was carried out in the same manner as in Example C27, except that 3.00 g of sodium propionate was used instead of lithium acetate.

Example C35

An operation was carried out in the same manner as in Example C27, except that 3.00 g of sodium octanoate was used instead of lithium acetate.

Example C36

An operation was carried out in the same manner as in Example C27, except that 3.00 g of sodium laurate was used instead of lithium acetate.

Example C37

An operation was carried out in the same manner as in Example C27, except that 3.00 g of sodium benzoate was used instead of lithium acetate.

Example C38

An operation was carried out in the same manner as in Example C27, except that 3.00 g of sodium succinate was used instead of lithium acetate.

Example C39

An operation was carried out in the same manner as in Example C27, except that 3.00 g of potassium hydrogen sulfate was used instead of lithium acetate.

Example C40

An operation was carried out in the same manner as in Example C27, except that 3.00 g of sodium hydrogen sulfate was used instead of lithium acetate.

Example C41

1.00 g of DHQ prepared as described above was dissolved in 9.00 g of 1-butanol to prepare a DHQ solution having a concentration of 10 weight %. Subsequently, 3.00 g of potassium acetate was added thereto, and the mixture was heated in an autoclave to carry out the dehydration reaction. The reaction temperature was 200 degrees centigrade, and the reaction time was 0.5 hours. After completion of the reaction, an insoluble matter was filtered using filter paper having a micro-pore diameter of 0.2 μm, and the residue was washed with ethanol. It was diluted with ethanol such that the total amount became 20.0 g. Then, the above-mentioned internal standard solution was added to 0.400 g of the diluted reaction solution, and the total amount was made up to 20 ml to give an analytical solution.

Example C42

An operation was carried out in the same manner as in Example C41, except that 3.00 g of rubidium acetate was used instead of potassium acetate.

Example C43

An operation was carried out in the same manner as in Example C41, except that 3.00 g of cesium acetate was used instead of potassium acetate.

Reference Example C1

An operation was carried out in the same manner as in Example C27, except that lithium acetate was not used.

Reference Example C2

An operation was carried out in the same manner as in Example C27, except that 0.300 g of sodium hydroxide (NaOH) was used instead of lithium acetate.

Reference Example C3

1.00 g of DHQ prepared as described above was dissolved in a mixed solvent of 1.30 g of methanol and 13.3 g of toluene to prepare a DHQ solution having a concentration of 6.40 weight %. Subsequently, 0.890 g (1 equivalent relative to DHQ) of trifluoroacetic acid was added thereto, and the mixture was heated to carry out the dehydration reaction. The reaction temperature was 100 degrees centigrade, and the reaction time was 2 hours. After completion of the reaction, the total amount of the reaction solution was recovered while it was diluted with ethanol, and the total amount was adjusted to be 20.0 g. The above-mentioned internal standard solution was added to 0.400 g of the diluted reaction solution, and the total amount was made up to 20 ml to give an analytical solution.

Reference Example C4

An operation was carried out in the same manner as in Example C1, except that the reaction temperature was changed to 80 degrees centigrade.

Reference Example C5

An operation was carried out in the same manner as in Example C1, except that the reaction temperature was changed to 100 degrees centigrade.

The results of Examples C1 to C5, and Reference Examples C1, C3 to C5 are shown in Table 7. The results of Examples C6 to C43, and Reference Example C2 are shown in Table 8.

TABLE 7

| | Catalyst | | | Reaction | | DHQ | | |
|---|---|---|---|---|---|---|---|---|
| | Type | Catalyst/DHQ (molar ratio) | Solvent | temperature (° C.) | Reaction time (hour) | Concentration (wt %) | Conversion rate (%) | Hydroquinone yield (%) |
| Example C1 | Sulfuric acid | 2 | Water | 120 | 4 | 6.4 | 98 | 54 |
| Example C2 | Sulfuric acid | 2 | Water | 170 | 4 | 6.4 | 98 | 56 |
| Example C3 | Sulfuric acid | 2 | Water | 120 | 8 | 2 | 96 | 54 |
| Example C4 | Sulfuric acid | 2 | Water | 180 | 8 | 2 | 100 | 62 |
| Example C5 | Sulfuric acid | 2 | Water | 200 | 8 | 2 | 100 | 65 |
| Ref. Example C1 | None | — | Water | 200 | 0.5 | 10 | 95 | 15 |
| Ref. Example C3 | Trifluoroacetic acid | 1 | Methanol/Toluene | 100 | 2 | 6.4 | 0 | 0 |
| Ref. Example C4 | Sulfuric acid | 2 | Water | 80 | 4 | 6.4 | 4 | 2 |
| Ref. Example C5 | Sulfuric acid | 2 | Water | 100 | 4 | 6.4 | 98 | 18 |

TABLE 8

| | Catalyst | | | Reaction | | DHQ | | |
|---|---|---|---|---|---|---|---|---|
| | Type | Catalyst/DHQ (weight ratio) | Solvent | temperature (° C.) | Reaction time (hour) | Concentration (wt %) | Conversion rate (%) | Hydroquinone yield (%) |
| Example C6 | zeolite Hβ | 3 | Water | 210 | 1 | 1 | 100 | 73 |
| Example C7 | zeolite Hβ | 3 | Acetonitrile | 180 | 1 | 2 | 100 | 82 |
| Example C8 | zeolite Hβ | 3 | Propionitrile | 200 | 1 | 2 | 100 | 75 |
| Example C9 | zeolite Hβ | 3 | Benzonitrile | 180 | 1 | 2 | 100 | 78 |
| Example C10 | zeolite Hβ | 3 | Dioxane | 180 | 1 | 2 | 100 | 74 |
| Example C11 | zeolite Hβ | 3 | MIBK | 180 | 1 | 2 | 100 | 80 |
| Example C12 | zeolite Hβ | 3 | Water | 200 | 0.5 | 10 | 100 | 64 |
| Example C13 | zeolite Hβ | 1 | Water | 200 | 0.5 | 10 | 100 | 60 |
| Example C14 | zeolite Hβ | 0.2 | Water | 200 | 8 | 2 | 100 | 54 |
| Example C15 | zeolite H-USY | 0.2 | Water | 200 | 8 | 2 | 100 | 56 |
| Example C16 | $Al_2O_3$ | 3 | Water | 200 | 1 | 1 | 100 | 62 |
| Example C17 | $Al_2O_3$ | 3 | Acetonitrile | 220 | 1 | 2 | 100 | 80 |
| Example C18 | $Al_2O_3$ | 3 | Propionitrile | 220 | 1 | 2 | 100 | 79 |
| Example C19 | $Al_2O_3$ | 3 | Benzonitrile | 220 | 1 | 2 | 100 | 86 |
| Example C20 | $Al_2O_3$ | 3 | MIBK | 180 | 1 | 2 | 100 | 69 |
| Example C21 | $Al_2O_3$ | 3 | 2-butanol | 200 | 0.5 | 10 | 98 | 51 |
| Example C22 | $Al_2O_3$ MSU-X | 0.2 | Water | 200 | 8 | 2 | 100 | 55 |
| Example C23 | $Al_2O_3$ MSU-X | 3 | Water | 200 | 0.5 | 1 | 100 | 62 |
| Example C24 | Activated clay | 3 | Water | 200 | 0.5 | 1 | 100 | 63 |
| Example C25 | montmorillonite K10 | 3 | Water | 200 | 0.5 | 1 | 100 | 58 |
| Example C26 | MgO | 1 | Water | 200 | 8 | 2 | 100 | 59 |
| Example C27 | lithium acetate | 3 | Water | 200 | 0.5 | 10 | 100 | 69 |
| Example C28 | sodium acetate | 1 | Water | 200 | 0.5 | 10 | 100 | 61 |
| Example C29 | sodium acetate | 3 | Water | 200 | 0.5 | 10 | 100 | 70 |
| Example C30 | potassium acetate | 3 | Water | 180 | 0.5 | 10 | 100 | 66 |
| Example C31 | potassium acetate | 3 | Water | 200 | 0.5 | 10 | 100 | 70 |
| Example C32 | rubidium acetate | 3 | Water | 200 | 0.5 | 10 | 100 | 72 |
| Example C33 | cesium acetate | 3 | Water | 200 | 0.5 | 10 | 100 | 63 |
| Example C34 | sodium propionate | 3 | Water | 200 | 0.5 | 10 | 100 | 71 |
| Example C35 | sodium octanoate | 3 | Water | 200 | 0.5 | 10 | 100 | 73 |
| Example C36 | sodium laurate | 3 | Water | 200 | 0.5 | 10 | 100 | 69 |
| Example C37 | sodium benzoate | 3 | Water | 200 | 0.5 | 10 | 100 | 54 |
| Example C38 | sodium succinate | 3 | Water | 200 | 0.5 | 10 | 100 | 65 |
| Example C39 | potassium hydrogen sulfate | 3 | Water | 200 | 0.5 | 10 | 100 | 66 |
| Example C40 | sodium hydrogen sulfate | 3 | Water | 200 | 0.5 | 10 | 100 | 60 |
| Example C41 | potassium acetate | 3 | 1-butanol | 200 | 0.5 | 10 | 100 | 57 |
| Example C42 | rubidium acetate | 3 | 1-butanol | 200 | 0.5 | 10 | 100 | 65 |
| Example C43 | cesium acetate | 3 | 1-butanol | 200 | 0.5 | 10 | 100 | 67 |
| Ref. Example C2 | NaOH | 0.3 | Water | 200 | 0.5 | 10 | 100 | 20 |

Example C44

1.00 g of DHQ prepared as described above and 0.310 g of sodium hydroxide were dissolved in 10.4 g of water to prepare a sodium salt (DHQ-Na) solution of 4-hydroxycyclohexane-1,3-dione having a concentration of 10.0 weight %. Subsequently, 0.400 g (0.8 molar ratio relative to DHQ-Na) of acetic acid was added thereto, and the mixture was heated to carry out the dehydration reaction. The reaction temperature was 200 degrees centigrade, and the reaction time was 0.5 hours. After completion of the reaction, the total amount of the reaction solution was recovered while it was diluted with the eluent described in the aforementioned analytical method 3, and the total amount was adjusted to be 20.0 g. The above-mentioned internal standard solution was added to 0.400 g of the diluted reaction solution, and the total amount was made up to 20 ml to give an analytical solution.

Example C45

An operation was carried out in the same manner as in Example C44, except that 0.800 g (1.1 molar ratio relative to DHQ-Na) of sulfuric acid was used instead of acetic acid.

Example C46

An operation was carried out in the same manner as in Example C44, except that 1.00 g (1.3 molar ratio relative to DHQ-Na) of sulfuric acid was used instead of acetic acid.

Example C47

An operation was carried out in the same manner as in Example C44, except that 1.10 g (1.4 molar ratio relative to DHQ-Na) of sulfuric acid was used instead of acetic acid.

Example C48

An operation was carried out in the same manner as in Example C44, except that 1.20 g (1.6 molar ratio relative to DHQ-Na) of sulfuric acid was used instead of acetic acid.

Example C49

An operation was carried out in the same manner as in Example C44, except that 0.200 g (0.3 molar ratio relative to DHQ-Na) of phosphoric acid was used instead of acetic acid.

Example C50

An operation was carried out in the same manner as in Example C44, except that 1.50 g (2.1 molar ratio relative to DHQ-Na) of phosphoric acid was used instead of acetic acid.

The results of Examples C44 to C50 are shown in Table 9.

TABLE 9

| | Catalyst | | | Reaction | | DHQ | | |
|---|---|---|---|---|---|---|---|---|
| | Type | Catalyst/DHQ-Na (molar ratio) | Solvent | temperature (° C.) | Reaction time (hour) | Concentration (wt %) | Conversion rate (%) | Hydroquinone yield (%) |
| Example C44 | Acetic acid | 0.8 | Water | 200 | 0.5 | 10 | 100 | 51 |
| Example C45 | Sulfuric acid | 1.1 | Water | 200 | 0.5 | 10 | 100 | 54 |
| Example C46 | Sulfuric acid | 1.3 | Water | 200 | 0.5 | 10 | 100 | 60 |
| Example C47 | Sulfuric acid | 1.4 | Water | 200 | 0.5 | 10 | 100 | 59 |
| Example C48 | Sulfuric acid | 1.6 | Water | 200 | 0.5 | 10 | 100 | 59 |
| Example C49 | Phosphoric acid | 0.3 | Water | 200 | 0.5 | 10 | 100 | 51 |
| Example C50 | Phosphoric acid | 2.1 | Water | 200 | 0.5 | 10 | 100 | 58 |

Example C51

10.0 g (61.7 mmol) of DOI was dissolved in 90.0 g of water, and stirred at 170 degrees centigrade for 2 hours in a 200-ml autoclave. The system was cooled down to room temperature (25 degrees centigrade) (a reaction solution A4). Separately, 0.910 g of 40% Ni/alumina (a product of JGC C&C) and 2.25 g (56.1 mmol) of sodium hydroxide (a product of Tosoh Corporation) were put into a 200-ml autoclave, and the system was replaced with nitrogen of 0.5 MPa three times. The total amount of the aforementioned reaction solution A4 was put into this reactor under a nitrogen stream. The atmosphere inside the reactor was replaced with hydrogen of 0.5 MPa three times, and then the hydrogen pressure inside the reactor was set to 2.5 MPa. The inside of the reactor was heated with stirring and the internal temperature was adjusted to be 50 degrees centigrade. After the reaction was carried out for 14 hours, the reactor was cooled until the temperature inside the reactor became near room temperature. Next, an insoluble matter was filtered (a filtrate B4) using filter paper having a micro-pore diameter of 1 μm. 20.9 g (34.8 mmol) of acetic acid was added to the filtrate B4, and put into the 200-ml autoclave again under a nitrogen stream. The reactor was heated until the internal temperature became 200 degrees centigrade, the reaction was carried out at that temperature for 0.5 hours, and then the reactor was cooled down to near room temperature (a reaction solution B4). The above-mentioned internal standard solution was added to 0.200 g of the reaction solution B4, and the total amount was made up to 20 ml to give an analytical solution. The quantitative analysis was carried out using the analysis conditions described in the aforementioned analytical method 3, thereby found that 4.07 g (3.70 mmol) of hydroquinone was produced, and hydroquinone was produced from DOI at a yield of 60%.

During the preparation of the reaction solution A4, the reaction solution after 0.5 hours was collected with stirring in the aforementioned autoclave, and it was confirmed by NMR that the compound represented by the formula (1) was contained. The $^1$H-NMR data and $^{13}$C-NMR data are shown in Example A.

It was confirmed by NMR that THB was contained in the reaction solution A4. The $^1$H-NMR data and $^{13}$C-NMR data are shown in Example A1.

Other aspects of the present invention are exemplified below. The first aspect relates to a method for producing 1,2,4-trihydroxybenzene as illustrated below.

[1] A method for producing 1,2,4-trihydroxybenzene from the compound represented by the above formula (1) by a dehydration reaction in the absence of an acid catalyst.

[2] The method for producing 1,2,4-trihydroxybenzene from the obtained compound represented by the above formula (1) according to [1], wherein the compound represented by the above formula (1) is produced from 2-deoxy-scylloinosose by a dehydration reaction in the absence of an acid catalyst.

[3] The method according to [1] or [2], wherein the dehydration reaction is carried out while the compound represented by the above formula (1) is dissolved in a reaction solvent and heated at equal to or more than 120 degrees centigrade.

[4] The method according to [3], wherein water is used as the reaction solvent.

[5] The method according to any one of [2] to [4], wherein 1,2,4-trihydroxybenzene is produced from 2-deoxy-scyllo-inosose in one-pot.

[6] A method for producing 1,2,4-trihydroxybenzene from 2,3,4,5-tetrahydroxy-cyclohexane-1-one by a dehydration reaction in the absence of an acid catalyst.

The second aspect relates to a method for producing hydroquinone as illustrated below.

[1] A method for producing hydroquinone comprising:
a step of heating 4-hydroxycyclohexane-1,3-dione in the presence of an aromatic compound,
wherein any one of the heated aromatic compound or 4-hydroxycyclohexane-1,3-dione forms a salt, and
the aforementioned aromatic compound has at least one or more hydroxyl groups bonded to an aromatic ring.

[2] The method according to [1], wherein the 4-hydroxycyclohexane-1,3-dione or the salt thereof is heated at equal to or more than 120 degrees centigrade.

[3] The method according to [1] or [2], wherein the aforementioned aromatic compound has two hydroxyl groups bonded to an aromatic ring.

[4] The method according to any one of [1] to [3], further comprising a step of either mixing of the aforementioned aromatic compound with a salt of 4-hydroxycyclohexane-1,3-dione, or mixing of a salt of the aforementioned aromatic compound with 4-hydroxycyclohexane-1,3-dione;
wherein, in the mixing step, hydroquinone or a salt thereof as the aforementioned aromatic compound or the salt thereof is mixed with 4-hydroxycyclohexane-1,3-dione or a salt thereof, and then the step of heating the 4-hydroxycyclohexane-1,3-dione or the salt thereof is carried out in the presence of the aforementioned aromatic compound or the salt thereof.

[5] The method according to [4], wherein, in the mixing step, hydroquinone obtained by carrying out the step of heating the 4-hydroxycyclohexane-1,3-dione or the salt thereof is mixed with the salt of 4-hydroxycyclohexane-1,3-dione.

[6] The method according to any one of [1] to [5], wherein the aforementioned 4-hydroxycyclohexane-1,3-dione is produced from 1,2,4-trihydroxybenzene by a catalytic hydrogenation reaction with the use of a metal catalyst containing an iron group element as a metal component.

[7] The method according to [6], wherein the iron group element is nickel or cobalt.

[8] The method according to [6] or [7], wherein the catalytic hydrogenation reaction is carried out with the use of a metal catalyst having the metal component supported in a carrier.

[9] The method according to [8], wherein alumina is used as the carrier.

[10] The method according to [6] or [7], wherein a Raney alloy is used as the aforementioned metal catalyst.

[11] The method according to any one of [1] to [10], wherein the 4-hydroxycyclohexane-1,3-dione salt is produced from the 1,2,4-trihydroxybenzene by a catalytic reduction reaction with the use of a metal catalyst in the presence of a basic compound.

[12] The method according to [11], wherein the aforementioned basic compound is any of an inorganic basic compound and an organic basic compound.

[13] The method according to [12], wherein the inorganic basic compound is selected from the group consisting of alkali metal, alkali earth metal, alkali metal hydroxide, alkali earth metal hydroxide and ammonium hydroxide.

[14] The method according to any one of [6] to [13], wherein the catalytic hydrogenation reaction is carried out with the use of an aqueous solution of 1,2,4-trihydroxybenzene.

[15] The method according to any one of [6] to [14], wherein the catalytic hydrogenation reaction is carried out with the use of 1 to 50 weight % of 1,2,4-trihydroxybenzene.

[16] The method according to any one of [6] to [15], wherein the catalytic hydrogenation reaction is carried out at 10 to 100 degrees centigrade.

[17] The method according to any one of [6] to [16];
wherein 1,2,4-trihydroxybenzene is produced through the following steps:
(a) a first step of producing a compound represented by the above formula (1) from 2-deoxy-scyllo-inosose by a dehydration reaction in the absence of an acid catalyst; and
(b) a second step of producing 1,2,4-trihydroxybenzene from the compound represented by the above formula (1) obtained in the first step by a dehydration reaction in the absence of an acid catalyst.

[18] A method for producing hydroquinone including a step of heating 4-hydroxycyclohexane-1,3-dione or a salt thereof at equal to or more than 120 degrees centigrade in the presence of a dehydration catalyst, wherein the dehydration catalyst is an oxide catalyst, or an acid or base catalyst represented by the following formula (2),

$$(M^a)_m X_n \quad (2)$$

wherein, in the formula (2), $M^a$ is $H^+$, $Li^+$, $Na^+$, $K^+$, $Rb^+$, $Cs^+$, $Be^{2+}$, $Mg^{2+}$, $Ca^{2+}$, $Sr^{2+}$ or $Ba^{2+}$; X is sulfate ion, hydrogen sulfate ion, sulfite ion, hydrogen sulfite ion, phosphate ion, hydrogen phosphate ion, dihydrogen phosphate ion, perchlorate ion, hexafluorophosphate ion, an anion of an aliphatic or aromatic carboxylic acid having 1 to 12 carbon atoms, or an anion of an aliphatic or aromatic sulfonic acid having 1 to 12 carbon atoms; an anion of an aliphatic or aromatic carboxylic acid having 1 to 12 carbon atoms and an anion of an aliphatic or aromatic sulfonic acid having 1 to 12 carbon atoms may be respectively immobilized on a carrier; m is 1 to 3; and n is 1 to 3.

[19] The method according to [18], wherein, in the step of heating 4-hydroxycyclohexane-1,3-dione or a salt thereof, 1 to 1,000 weight parts of the dehydration catalyst is used, based on 100 weight parts of the 4-hydroxycyclohexane-1,3-dione or the salt thereof.

[20] The method according to [18] or [19], wherein, in the step of heating 4-hydroxycyclohexane-1,3-dione or a salt thereof, the 4-hydroxycyclohexane-1,3-dione or the salt thereof is heated in water.

[21] The method according to [18] or [19], wherein, in the step of heating 4-hydroxycyclohexane-1,3-dione or a salt thereof, the 4-hydroxycyclohexane-1,3-dione or the salt thereof is heated in an organic solvent, and the organic solvent is selected from the group consisting of an aliphatic alcohol having 2 to 12 carbon atoms, an aliphatic nitrile having 1 to 12 carbon atoms, an aromatic nitrile, an alicyclic ether having 1 to 12 carbon atoms and a dialkyl ketone having 1 to 12 carbon atoms.

[22] The method according to any one of [18] to [21], wherein the dehydration catalyst is an oxide catalyst.

[23] The method according to [22], wherein the oxide catalyst contains any of aluminum and silicon.

[24] The method according to [23], wherein the oxide catalyst is a solid acid catalyst containing a compound represented by the following formula (3),

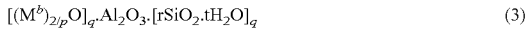

$$[(M^b)_{2/p}O]_q \cdot Al_2O_3 \cdot [rSiO_2 \cdot tH_2O]_q \quad (3)$$

wherein, in the formula (3), $M^b$ is a metal atom selected from the group consisting of Na, K, Ca and Ba; p is 1 or 2; q is 0 or 1; r is 2 to 10; and t is 2 to 7.

[25] The method according to any one of [18] to [21], wherein the dehydration catalyst is an acid or base catalyst represented by the above formula (2).

[26] The method according to [25], wherein the dehydration catalyst is a base catalyst represented by the above formula (2).

[27] The method according to any one of [18] to [26], wherein the 4-hydroxycyclohexane-1,3-dione or the salt thereof is produced through the following steps:
(a) a first step of producing a compound represented by the above formula (1) from 2-deoxy-scyllo-inosose by a dehydration reaction in the absence of an acid catalyst;
(b) a second step of producing 1,2,4-trihydroxybenzene from the compound represented by the above formula (1) obtained in the first step by a dehydration reaction in the absence of an acid catalyst; and
(c) a third step of producing 4-hydroxycyclohexane-1,3-dione or a salt thereof from the 1,2,4-trihydroxybenzene obtained in the second step by a catalytic hydrogenation reaction with the use of an iron group metal catalyst.

The present application claims priority based on Japanese patent application No. 2009-108995 filed on Apr. 28, 2009, Japanese patent application No. 2009-135380 filed on Jun. 4, 2009, and Japanese patent application No. 2009-135375 filed on Jun. 4, 2009, and incorporates herein the entire disclosure thereof by reference.

The invention claimed is:

1. A method for producing hydroquinone from 2-deoxy-scyllo-inosose, comprising the following steps (a) to (d):
(a) a first step of producing a compound represented by the following formula (1) from 2-deoxy-scyllo-inosose by a dehydration reaction;
(b) a second step of producing 1,2,4-trihydroxybenzene from the compound represented by said formula (1) obtained in said first step by a dehydration reaction;
(c) a third step of producing 4-hydroxycyclohexane-1,3-dione or a salt thereof from the 1,2,4-trihydroxybenzene by a catalytic hydrogenation reaction with the use of a metal catalyst; and
(d) a fourth step of producing hydroquinone by heating the 4-hydroxycyclohexane-1,3-dione or the salt thereof

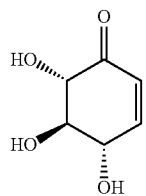

(1)

2. The method according to claim 1, wherein, in said second step, the 1,2,4-trihydroxybenzene is produced from the compound represented by said formula (1) in the absence of an acid catalyst.

3. The method according to claim 2, wherein, in said first step, the compound represented by said formula (1) is produced from 2-deoxy-scyllo-inosose in the absence of an acid catalyst.

4. The method according to claim 2, wherein, in said second step, the dehydration reaction is carried out while the compound represented by said formula (1) is dissolved in a reaction solvent and heated at equal to or more than 120 degrees centigrade.

5. The method according to claim 4, wherein water is used as said reaction solvent.

6. The method according to claim 2, wherein the dehydration reaction in said first step and the dehydration reaction in said second step are carried out in one-pot.

7. The method according to claim 1, wherein said fourth step comprises heating 4-hydroxycyclohexane-1,3-dione in the presence of an aromatic compound,
one of said heated aromatic compound or 4-hydroxycyclohexane-1,3-dione forms a salt, and
said aromatic compound has at least one or more hydroxyl groups bonded to an aromatic ring.

8. The method according to claim 7, wherein, in said fourth step, the 4-hydroxycyclohexane-1,3-dione or the salt thereof is heated at equal to or more than 120 degrees centigrade.

9. The method according to claim 7, wherein said aromatic compound has two hydroxyl groups bonded to an aromatic ring.

10. The method according to claim 7, wherein said fourth step further comprises either mixing of said aromatic compound with a salt of 4-hydroxycyclohexane-1,3-dione, or mixing of a salt of said aromatic compound with 4-hydroxycyclohexane-1,3-dione, and
in said mixing, hydroquinone or a salt thereof as said aromatic compound or the salt thereof is mixed with 4-hydroxycyclohexane-1,3-dione or a salt thereof, and then the 4-hydroxycyclohexane-1,3-dione or the salt thereof is heated in the presence of said aromatic compound or the salt thereof.

11. The method according to claim 10, wherein, in said mixing, hydroquinone obtained by heating the 4-hydroxycyclohexane-1,3-dione or the salt thereof is mixed with a salt of 4-hydroxycyclohexane-1,3-dione.

12. The method according to claim 7, wherein said metal catalyst contains an iron group element as a metal component, and
in said third step, 4-hydroxycyclohexane-1,3-dione is produced from the 1,2,4-trihydroxybenzene by a catalytic hydrogenation reaction with the use of said metal catalyst containing said iron group element as a metal component.

13. The method according to claim 12, wherein said iron group element is nickel or cobalt.

14. The method according to claim 12, wherein, in said third step, the catalytic hydrogenation reaction is carried out with the use of a metal catalyst having said metal component supported on a carrier.

15. The method according to claim 14, wherein, in said third step, alumina is used as said carrier.

16. The method according to claim 12, wherein, in said third step, a Raney alloy is used as said metal catalyst.

17. The method according to claim 13, wherein, in said third step, 4-hydroxycyclohexane-1,3-dione salt is produced from the 1,2,4-trihydroxybenzene by a catalytic hydrogenation reaction with the use of said metal catalyst in the presence of a basic compound.

18. The method according to claim 17, wherein said basic compound is an inorganic basic compound.

19. The method according to claim 18, wherein said inorganic basic compound is selected from the group consisting of alkali metal, alkali earth metal, alkali metal hydroxide, alkali earth metal hydroxide and ammonium hydroxide.

20. The method according to claim 17, wherein, in said third step, 4-hydroxycyclohexane-1,3-dione salt is produced from the 1,2,4-trihydroxybenzene by a catalytic hydrogenation reaction with the use of an aqueous solution of 1,2,4-trihydroxybenzene.

21. The method according to claim 12, wherein, in said third step, the catalytic hydrogenation reaction is carried out with the use of 1,2,4-trihydroxybenzene in a solvent in an amount of equal to or more than 1 weight % and equal to or less than 50 weight % of the solution.

22. The method according to claim 12, wherein, in said third step, the catalytic hydrogenation reaction is carried out at equal to or more than 10 degrees centigrade and equal to or less than 100 degrees centigrade.

23. The method according to claim 12, wherein, in said first step, the compound represented by said formula (1) is produced from 2-deoxy-scyllo-inosose by a dehydration reaction in the absence of an acid catalyst, and in said second step, 1,2,4-trihydroxybenzene is produced from the compound represented by said formula (1) obtained in said first step by a dehydration reaction in the absence of an acid catalyst.

24. The method according to claim 1, wherein said fourth step comprises heating 4-hydroxycyclohexane-1,3-dione or a salt thereof at equal to or more than 120 degrees centigrade in the presence of a dehydration catalyst, and said dehydration catalyst is an oxide catalyst, or an acid or base catalyst represented by the following formula (2), $$(M^a)_m X_n \quad (2)$$

wherein, in the formula (2), $M^a$ is $H^+$, $Li^+$, $Na^+$, $K^+$, $Rb^+$, $Cs^+$, $Be^{2+}$, $Mg^{2+}$, $Ca^{2+}$, $Sr^{2+}$ or $Ba^{2+}$; X is sulfate ion, hydrogen sulfate ion, sulfite ion, hydrogen sulfite ion, phosphate ion, hydrogen phosphate ion, dihydrogen phosphate ion, perchlorate ion, hexafluorophosphate ion, an anion of an aliphatic or aromatic carboxylic acid having 1 to 12 carbon atoms, or an anion of an aliphatic or aromatic sulfonic acid having 1 to 12 carbon atoms; an anion of an aliphatic or aromatic carboxylic acid having 1 to 12 carbon atoms and an anion of an aliphatic or aromatic sulfonic acid having 1 to 12 carbon atoms may be respectively immobilized on a carrier; m is 1 to 3; and n is 1 to 3.

25. The method according to claim 24, wherein, in said heating 4-hydroxycyclohexane-1,3-dione or a salt thereof, the dehydration catalyst is used in an amount of equal to or more than 1 weight part and equal to or less than 1,000 weight parts, based on 100 weight parts of the 4-hydroxycyclohexane-1,3-dione or the salt thereof.

26. The method according to claim 24, wherein, in said heating 4-hydroxycyclohexane-1,3-dione or a salt thereof, the 4-hydroxycyclohexane-1,3-dione or the salt thereof is heated in water.

27. The method according to claim 24, wherein, in said heating 4-hydroxycyclohexane-1,3-dione or a salt thereof, the 4-hydroxycyclohexane-1,3-dione or the salt thereof is heated in an organic solvent, and said organic solvent is selected from the group consisting of an aliphatic alcohol having 2 to 12 carbon atoms, an aliphatic nitrile having 2 to 12 carbon atoms, an aromatic nitrile, an aliphatic or alicyclic ether having 2 to 12 carbon atoms and a dialkyl ketone having 3 to 12 carbon atoms.

28. The method according to claim 24, wherein said dehydration catalyst is an oxide catalyst.

29. The method according to claim 28, wherein said oxide catalyst contains any of aluminum and silicon.

30. The method according to claim 29, wherein said oxide catalyst is a solid acid catalyst having a compound represented by the following formula (3), $$[(M^b)_{2/p}O]_q \cdot Al_2O_3 \cdot [rSiO_2 \cdot tH_2O]_q \quad (3)$$

wherein, in the formula (3), $M^b$ is a metal atom selected from the group consisting of Na, K, Ca and Ba; p is 1 or 2; q is 0 or 1; r is 2 to 10; and t is 2 to 7.

31. The method according to claim 27, wherein said dehydration catalyst is an acid or base catalyst represented by said formula (2).

32. The method according to claim 31, wherein said dehydration catalyst is a base catalyst represented by said formula (2).

33. The method according to claim 24, wherein, in said first step, the compound represented by said formula (1) is produced from 2-deoxy-scyllo-inosose by a dehydration reaction in the absence of an acid catalyst, in said second step, 1,2,4-trihydroxybenzene is produced from the compound represented by said formula (1) obtained in said first step by a dehydration reaction in the absence of an acid catalyst, and in said third step, 4-hydroxycyclohexane-1,3-dione or a salt thereof is produced from the 1,2,4-trihydroxybenzene obtained in said second step by a catalytic hydrogenation reaction with the use of an iron group metal catalyst

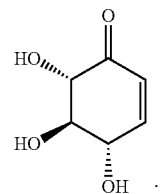

(1)

34. A method for producing 1,2,4-trihydroxybenzene from a compound represented by the following formula (1) by a dehydration reaction in the absence of an acid catalyst

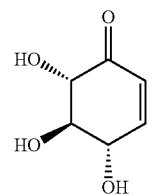

(1)

35. A method for producing hydroquinone comprising heating 4-hydroxycyclohexane-1,3-dione in the presence of an aromatic compound, wherein one of said heated aromatic compound or 4-hydroxycyclohexane-1,3-dione forms a salt, and said aromatic compound has at least one or more hydroxyl groups bonded to an aromatic ring.

36. A method for producing hydroquinone comprising heating 4-hydroxycyclohexane-1,3-dione or a salt thereof at equal to or more than 120 degrees centigrade in the presence of a dehydration catalyst, wherein said dehydration catalyst is an oxide catalyst, an acid or base catalyst represented by the following formula (2), $$(M^a)_m X_n \quad (2)$$

wherein, in the formula (2), $M^a$ is $H^+$, $Li^+$, $Na^+$, $K^+$, $Rb^+$, $Cs^+$, $Be^{2+}$, $Mg^{2+}$, $Ca^{2+}$, $Sr^{2+}$ or $Ba^{2+}$; X is sulfate ion, hydrogen sulfate ion, sulfite ion, hydrogen sulfite ion, phosphate ion, hydrogen phosphate ion, dihydrogen phosphate ion, perchlorate ion, hexafluorophosphate ion, an anion of an aliphatic or aromatic carboxylic acid having 1 to 12 carbon atoms, or an anion of an aliphatic or aromatic sulfonic acid having 1 to 12 carbon atoms; an anion of an aliphatic or aromatic carboxylic acid having 1 to 12 carbon atoms and an anion of an aliphatic or aromatic sulfonic acid having 1 to 12 carbon atoms may be respectively immobilized on a carrier; m is 1 to 3; and n is 1 to 3.

* * * * *